United States Patent
Ha et al.

(10) Patent No.: US 9,931,026 B2
(45) Date of Patent: Apr. 3, 2018

(54) BALLOON CATHETER WITH IMAGE CAPTURE AND LIGHT EMISSION FEATURES

(71) Applicant: Acclarent, Inc., Menlo Park, CA (US)

(72) Inventors: Hung V. Ha, San Jose, CA (US); Ketan P. Muni, San Jose, CA (US); Andy Nguyen, San Jose, CA (US); Randy S. Chan, San Jose, CA (US)

(73) Assignee: ACCLARENT, INC., Irvine, CA (US)

( * ) Notice: Subject to any disclaimer, the term of this patent is extended or adjusted under 35 U.S.C. 154(b) by 117 days.

(21) Appl. No.: 14/826,412

(22) Filed: Aug. 14, 2015

(65) Prior Publication Data

US 2016/0287059 A1 Oct. 6, 2016

Related U.S. Application Data

(60) Provisional application No. 62/139,933, filed on Mar. 30, 2015.

(51) Int. Cl.
*A61B 1/00* (2006.01)
*A61B 1/04* (2006.01)
(Continued)

(52) U.S. Cl.
CPC ............ *A61B 1/05* (2013.01); *A61B 1/00082* (2013.01); *A61B 1/00094* (2013.01); *A61B 1/00135* (2013.01); *A61B 1/04* (2013.01); *A61B 1/0684* (2013.01); *A61B 1/07* (2013.01); *A61B 1/227* (2013.01); *A61B 1/233* (2013.01); *A61B 1/32* (2013.01); *A61M 25/10* (2013.01);
(Continued)

(58) Field of Classification Search
CPC ......... A61B 1/005; A61B 1/05; A61B 1/0684; A61B 1/07; A61B 1/227; A61B 1/32; A61B 1/00094; A61B 1/00135
See application file for complete search history.

(56) References Cited

U.S. PATENT DOCUMENTS

| 6,066,090 A | 5/2000 | Yoon |
| 6,716,813 B2 | 4/2004 | Lim et al. |

(Continued)

FOREIGN PATENT DOCUMENTS

| WO | WO 2013/0122056 | 8/2013 | |
| WO | WO-2013122056 A1 * | 8/2013 | ......... A61B 1/00082 |

(Continued)

OTHER PUBLICATIONS

English Translation, WO 2013/122056 from AIPN, 55 pages.*

(Continued)

*Primary Examiner* — Timothy J Neal
(74) *Attorney, Agent, or Firm* — Frost Brown Todd LLC.

(57) ABSTRACT

A dilation catheter system comprises a guide member, a dilation catheter, and an image sensor. The guide member includes a shaft comprising a distal end and a proximal end. The shaft defines a longitudinal axis. The dilation catheter comprises an expandable dilator and is movable relative to the guide member. The expandable dilator is sized to fit within one or both of a Eustachian tube or a passageway associated with a paranasal sinus. The image sensor is configured to provide visualization within anatomy of a patient. The image sensor is integral with the dilation catheter.

11 Claims, 16 Drawing Sheets

(51) Int. Cl.
*A61B 1/05* (2006.01)
*A61B 1/06* (2006.01)
*A61B 1/07* (2006.01)
*A61B 1/227* (2006.01)
*A61B 1/32* (2006.01)
*A61B 1/233* (2006.01)
*A61M 25/10* (2013.01)
*A61M 29/02* (2006.01)
*A61M 25/06* (2006.01)

(52) U.S. Cl.
CPC ..... *A61M 29/02* (2013.01); *A61M 2025/0681* (2013.01); *A61M 2210/0675* (2013.01)

(56) References Cited

U.S. PATENT DOCUMENTS

| | | |
|---|---|---|
| 8,888,686 B2 | 11/2014 | Drontle et al. |
| 8,992,420 B2 | 3/2015 | Maahs et al. |
| 9,155,492 B2 | 10/2015 | Jenkins et al. |
| 9,289,582 B2 | 3/2016 | Suehara |
| 2003/0212373 A1* | 11/2003 | Hall ................ A61M 25/0668 604/263 |
| 2004/0199053 A1* | 10/2004 | Boulais ............... A61B 1/0005 600/146 |
| 2005/0154262 A1* | 7/2005 | Banik ............... A61B 1/00059 600/179 |
| 2006/0004323 A1 | 1/2006 | Chang et al. |
| 2006/0063973 A1* | 3/2006 | Makower ......... A61B 1/00135 600/114 |
| 2007/0225750 A1* | 9/2007 | Ren ..................... A61F 2/013 606/200 |
| 2008/0172033 A1 | 7/2008 | Keith et al. |
| 2010/0030031 A1 | 2/2010 | Goldfarb et al. |
| 2010/0274188 A1 | 10/2010 | Chang et al. |
| 2011/0004057 A1 | 1/2011 | Goldfarb et al. |
| 2012/0238805 A1 | 9/2012 | Iwasaka et al. |
| 2013/0274715 A1* | 10/2013 | Chan .................. A61M 25/10 604/514 |
| 2014/0261545 A1 | 9/2014 | Jenkins et al. |
| 2014/0261579 A1 | 9/2014 | Jenkins et al. |
| 2015/0196738 A1 | 7/2015 | Yamazaki et al. |
| 2015/0374963 A1 | 12/2015 | Chan et al. |

FOREIGN PATENT DOCUMENTS

| | | |
|---|---|---|
| WO | WO 2014/0050620 | 4/2014 |
| WO | WO 2014/050620 A1 | 4/2014 |

OTHER PUBLICATIONS

U.S. Appl. No. 62/139,933, filed Mar. 30, 2015.
U.S. Appl. No. 62/140,104, filed Mar. 30, 2015.
International Search Report dated Jun. 30, 2016 re Application No. PCT/US2016/024728.
St. Croix, B., et al., "Genes Expressed in Human Tumor Endothelium," Science, Aug. 18, 2000, 289(5482):1197-1201, 6 pgs.
Written Opinion dated Jun. 30, 2016 for Application No. PCT/US2016/024728, 5 pgs.
International Search Report and Written Opinion dated Aug. 19, 2016 for Application No. PCT/US2016/024716, 16 pgs.
U.S. Office Action, Non-Final, dated Jul. 20, 2017 for U.S. Appl. No. 14/826,400, 15 pgs.

\* cited by examiner

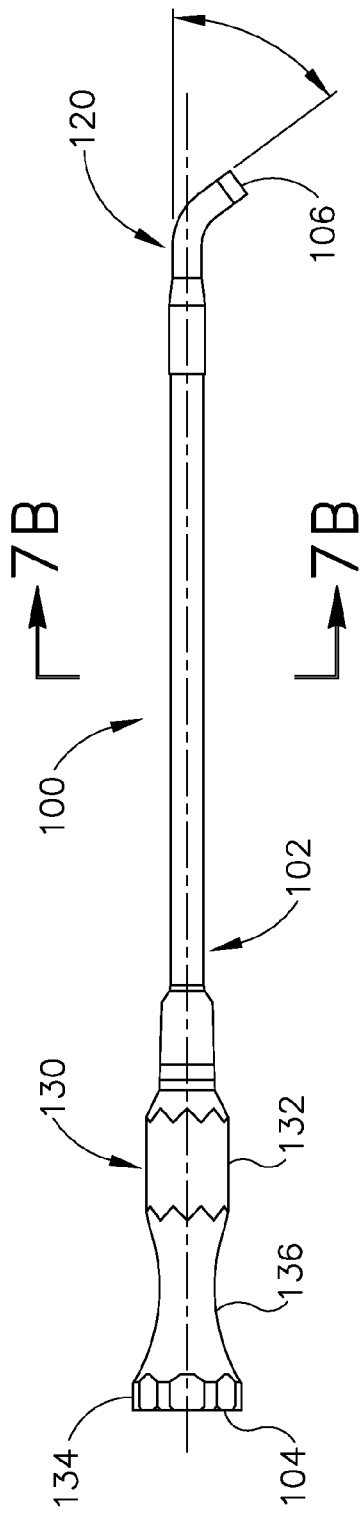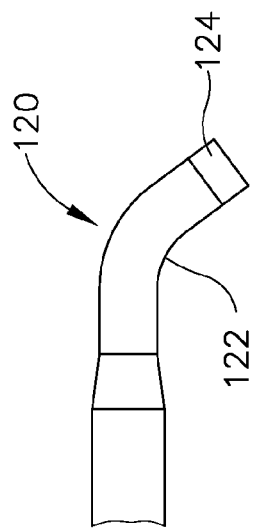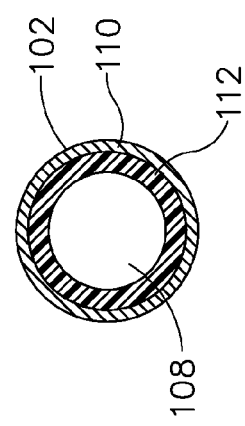
Fig.7A
Fig.7B
Fig.8

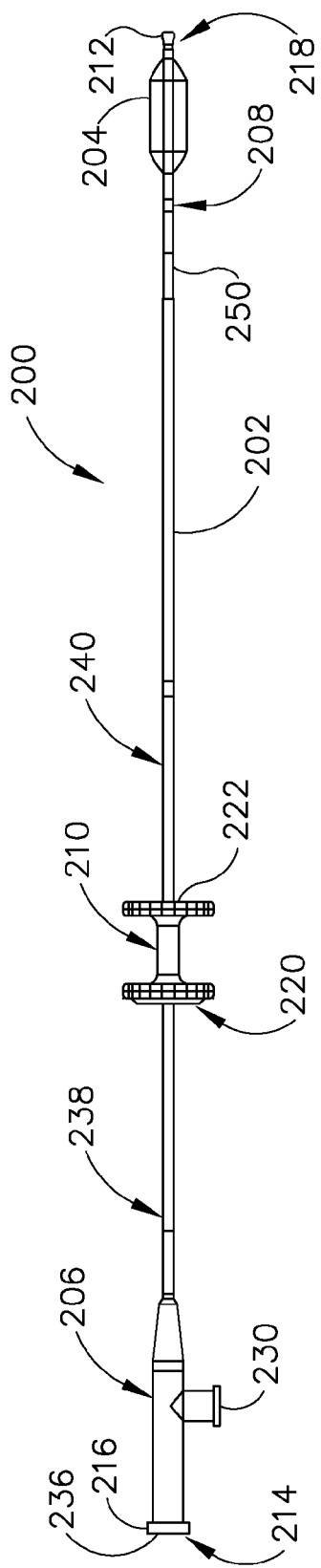
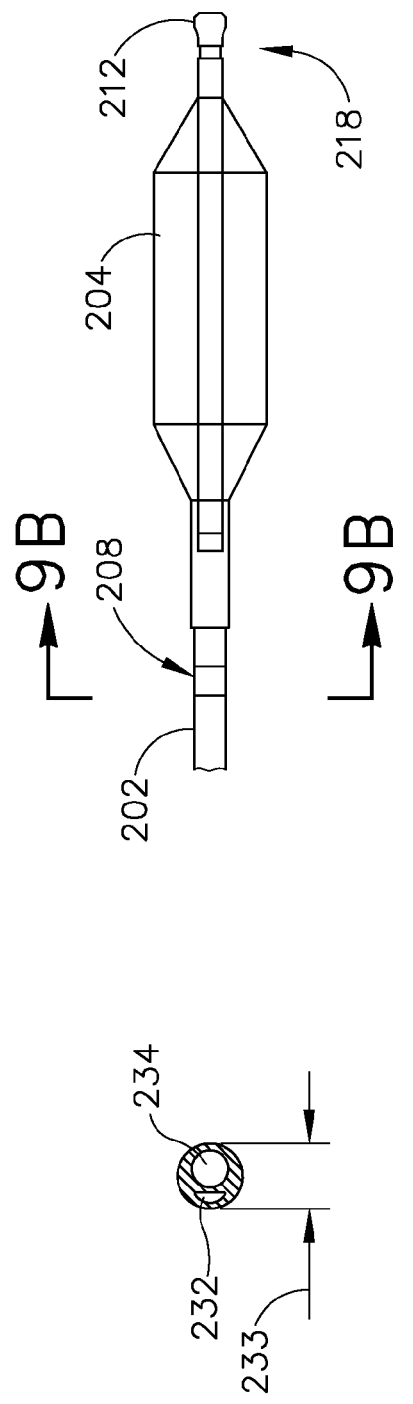
Fig.9A
Fig.9B
Fig.10

BALLOON CATHETER WITH IMAGE CAPTURE AND LIGHT EMISSION FEATURES

PRIORITY

This application claims priority to U.S. Provisional Patent App. No. 62/139,933, entitled "Balloon Catheter with Image Capture and Light Emission Features," filed Mar. 30, 2015, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide catheter to position an dilation catheter within the anatomical passageway, then inflating a balloon disposed on the dilation catheter with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

Alternatively such dilation catheters may also be employed using a similar method for the dilation of a Eustachian tube located adjacent to the paranasal sinus of a patent. A system that may be used to perform such procedures may be provided in accordance with the teachings of U.S. patent application Ser. No. 14/317,269, entitled "Vent Cap for a Eustachian Tube Dilation System," filed Jun. 29, 2014, the disclosure of which is incorporated by reference herein.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. Alternatively, it may be desirable to eliminate the endoscope altogether when patient anatomy proves too small and/or tortuous for full visualization using such an endoscope. In either case, this may be accomplished using imaging sensors positioned on either the guide catheter or the balloon catheter, or both the guide catheter and the dilation catheter. Such imaging sensors may be positioned within or near to the target area and be used to visualize the target area.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 7A depicts a side elevational view of an exemplary guide catheter;

FIG. 7B depicts a cross-sectional view of a shaft of the guide catheter of FIG. 7A, taken along line 7B-7B of FIG. 7A;

FIG. 8 depicts a detailed side elevational view of the distal end of the guide catheter of FIG. 7A;

FIG. 9A depicts a side elevational view of an exemplary dilation catheter for use with the guide catheter of FIG. 7A;

FIG. 9B depicts a cross-sectional view of a shaft of the dilation catheter of FIG. 9A, taken along line 9B-9B of FIG. 10;

FIG. 10 depicts a detailed side elevational view of the distal end of the dilation catheter of FIG. 9A;

Figure 1:
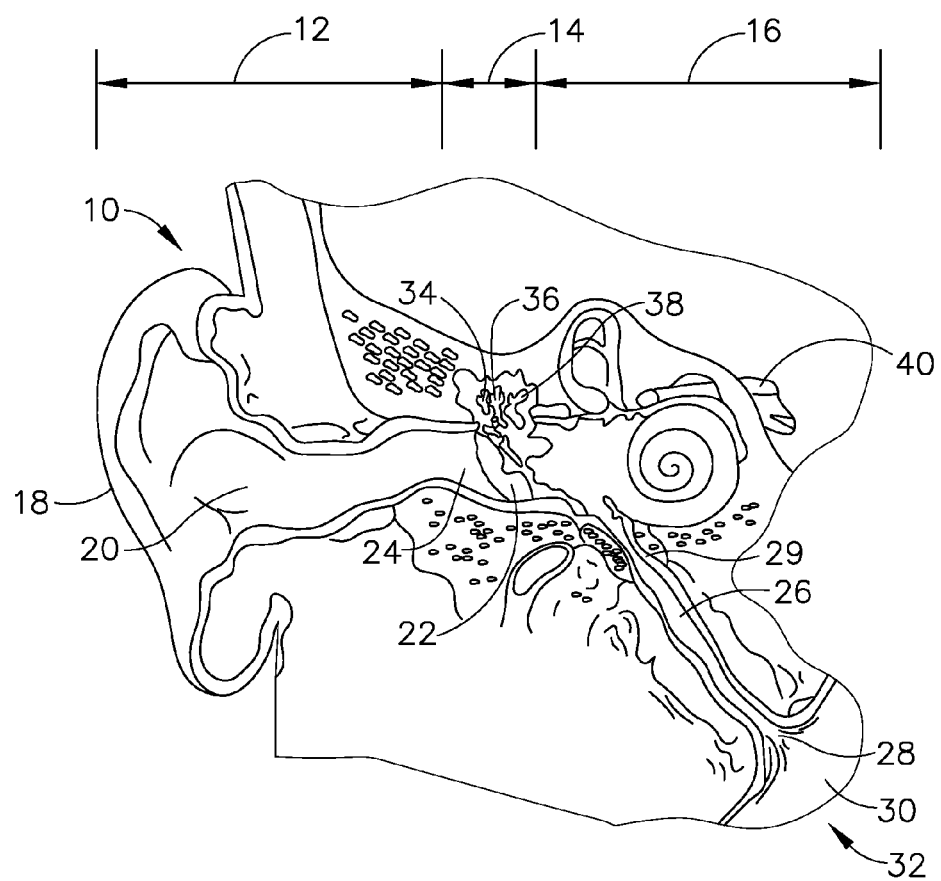
FIG. 1 depicts a cross-sectional view of an ear, with an inner, middle and outer ear portions and a Eustachian tube connecting the middle ear with a nasopharynx region.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Eustachian Tube Treatment Procedures

Figure 2:
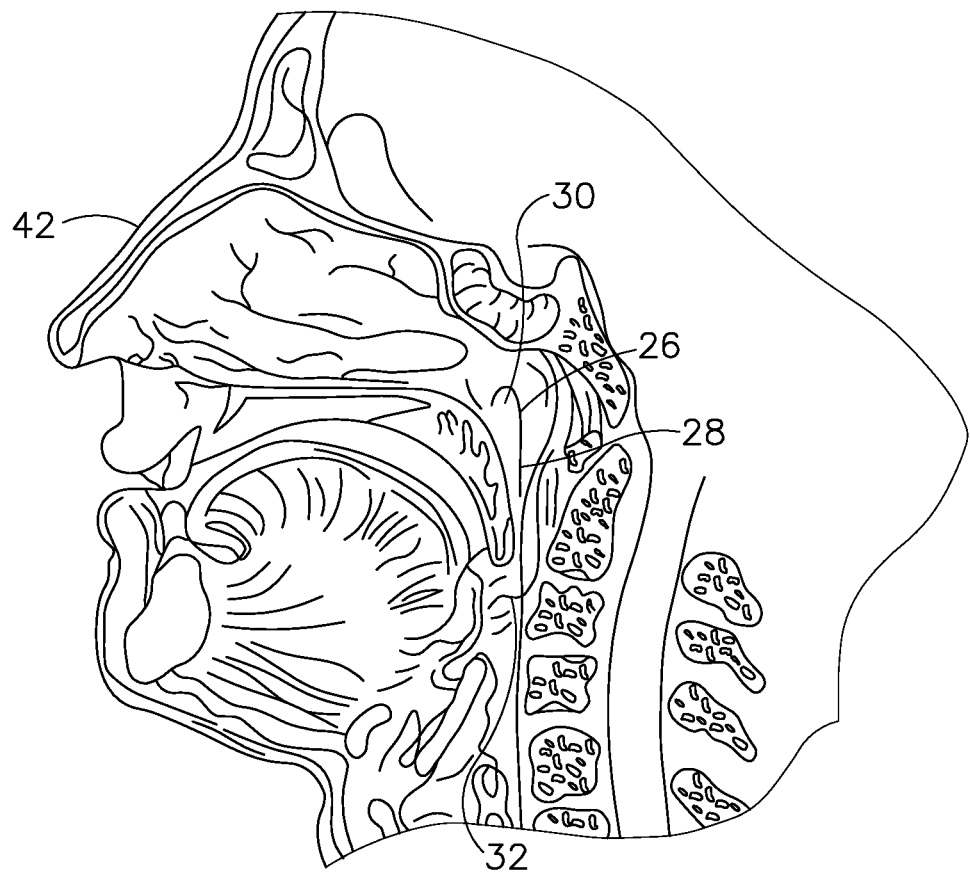
FIG. 2 depicts a cross-sectional view of a head, with the nasopharynx region of FIG. 1 fully visible.

FIGS. 1 and 2 show an ear (10) comprising three parts: an external ear (12), a middle ear (14) and an inner ear (16). External ear (12) includes an auricle (18) and an ear canal (20) that gather sound and direct it towards a tympanic membrane (22) (also referred to as the eardrum) located at an inner end (24) of the ear canal (20). Middle ear (14) lies between the external and inner ears (12) and (16) and is connected to the back of the throat by a Eustachian tube (26) which serves as a pressure equalizing valve between ear (10) and the sinuses. Eustachian tube (26) terminates in an opening or ostium (28) in the nasopharynx region (30) of the throat (32). In addition to tympanic membrane (22), middle ear (14) also includes three small ear bones (ossicles): a malleus (34) (hammer), an incus (36) (anvil) and a stapes (38) (stirrup). These bones (34, 36, 38) transmit sound vibrations to inner ear (16) and thereby act as a transformer, converting sound vibrations in canal (20) of external ear (12) into fluid waves in inner ear (16). These fluid waves stimulate several nerve endings (40) that, in turn, transmit sound energy to the brain where it is interpreted.

Eustachian tube (26) is shown as a narrow, two to two-and-a-half centimeter long channel, measured from ostium (28) to isthmus (29), connecting middle ear (14) with nasopharynx (30). Eustachian tube (26) functions as a pressure equalizing valve for middle ear (14), which is normally filled with air. Typically, Eustachian tube (26) opens for a fraction of a second periodically in response to swallowing or yawning. In so doing, it allows air into middle ear (14) to replace air that has been absorbed by the middle ear lining (mucous membrane) or to equalize pressure changes occurring on altitude changes. Anything that interferes with this periodic opening and closing of Eustachian tube (26) may result in hearing impairment or other ear symptoms.

Obstruction or blockage of Eustachian tube (26) results in a negative middle ear pressure (14), with retraction (sucking in) of tympanic membrane (22). In adults, this may be accompanied by some ear discomfort, a fullness or pressure feeling, and may result in a mild hearing impairment and/or head noise (tinnitus). There may be no symptoms in children. If the obstruction is prolonged, fluid may be drawn from the mucous membrane of middle ear (14), creating a condition referred to as serous otitis media (fluid in the middle ear). This may occur in children in connection with an upper respiratory infection and may account for hearing impairment associated with this condition.

A lining membrane (mucous membrane) of middle ear (14) and Eustachian tube (26) is connected with, and is the same as, the membrane of nose (42), sinuses (not shown) and throat (32). Infection of these areas results in mucous membrane swelling, which in turn may result in obstruction of Eustachian tube (26). This may ultimately result in acute or chronic serous otitis media, with fluid accumulating in middle ear (14). In the presence of bacteria, this fluid may become infected, leading to what may be referred to as an acute suppurative otitis media (infected or abscessed middle ear). When infection does not develop, the fluid remains until Eustachian tube (26) again begins to function normally, at which time the fluid is absorbed or drains down the Eustachian tube (26) into throat (32) through Eustachian tube ostium (28).

Chronic serous otitis media may result from longstanding Eustachian tube blockage, or from thickening of the fluid so that it cannot be absorbed or drained down Eustachian tube (26). Under some circumstances, this chronic condition may be associated with hearing impairment. There may also be recurrent ear pain. Fortunately, serous otitis media may persist for many years without producing any permanent damage to middle ear (14). The presence of fluid in middle ear (14), however, makes it very susceptible to recurrent acute infections. These recurrent infections may result in middle ear damage.

When Eustachian tube (26) contains a build-up of fluid, a number of things may occur. First, the body may absorb the air from middle ear (14), thus causing a vacuum to form. Such a vacuum may tend pull the lining membrane and ear drum (22) inwardly, causing pain. Next, the body may replace the vacuum with more fluid, which may tend to relieve pain, but the patient may experience a fullness sensation in ear (10). Treatment of this condition with antihistamines and decongestants can take many weeks to be fully effective. Finally, the fluid may become infected, which may be painful and may lead to other conditions associated with such an infection such as fever and/or hearing loss or degradation. If inner ear (14) is affected by such an infection, the patient may experience dizziness or disorientation— symptoms typically associated with the condition of vertigo.

Although the above described symptoms may be treated with antihistamines, decongestants, and antibiotics, such pharmaceuticals may be less desirable because they may not produce immediate resolution of symptoms caused by buildup of fluid in middle ear (14). Thus, immediate relief may be achieved by simply removing the fluid from Eustachian tube (26). Moreover, while administration of the pharmaceuticals described above may eventually resolve the infection, such treatment may not resolve the underlying issue of improper functioning of Eustachian tube (26). Accordingly, it may be desirable to perform surgical treatments of chronic serous otitis media to both achieve immediate relief of symptoms and to resolve any underling issues with Eustachian tube (26) function.

Figure 3:
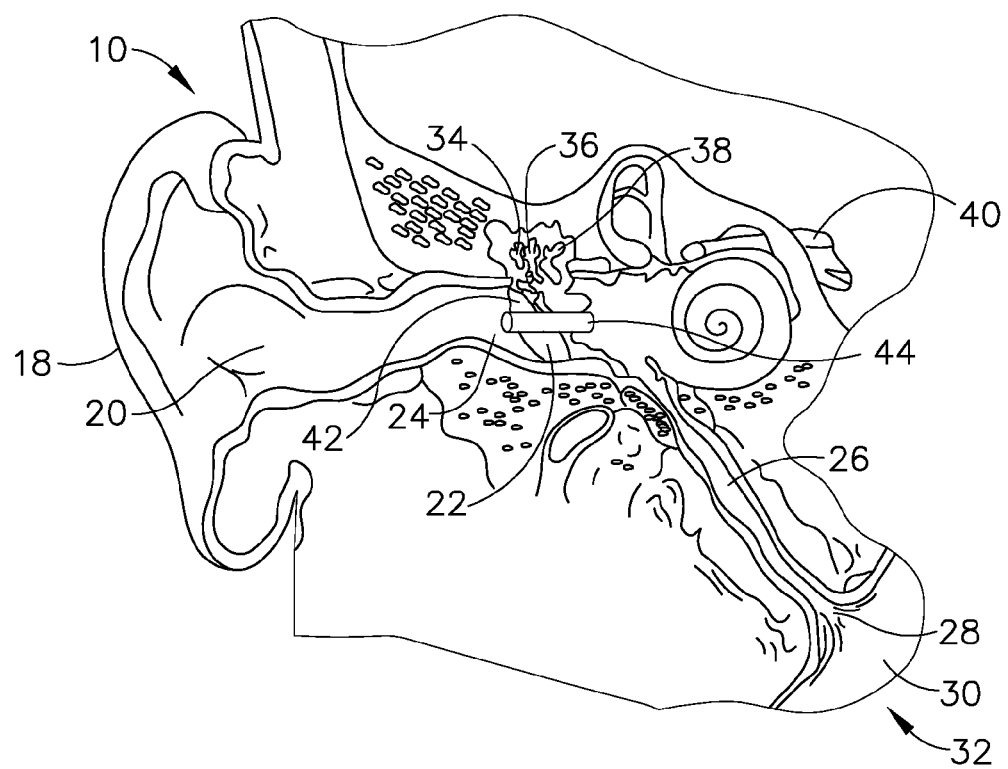
FIG. 3 depicts a cross-sectional view of the ear of FIG. 1, with a ventilation tube inserted within an incision in an eardrum.

FIG. 3 shows a myringotomy procedure, which may be performed to relieve fluid in middle ear (14). For instance, an incision (42) may be formed in tympanic membrane (22) to drain or remove fluid from middle ear (14). A hollow plastic tube (44) may be inserted and/or lodged in incision (42) to prevent incision (42) from self-sealing, thereby maintaining ventilation of middle ear (14) over an extended period of time. Thus during a treatment period, ventilation tube (44) temporarily takes the place of the Eustachian tube (26), performing the function of equalizing the pressure in middle ear (14). In some instances, the treatment period may last for a period of three to nine months. Such a period may permit the Eustachian tube (26) blockage to subside. After the treatment period, ventilation tube (44) may naturally dislodge and tympanic membrane (22) may self-seal. Alternatively, ventilation tube (44) may be removed surgically by a medical professional. Regardless of how ventilation tube (44) is removed, Eustachian tube (26) may resume its typical function after the treatment period.

Figure 4:
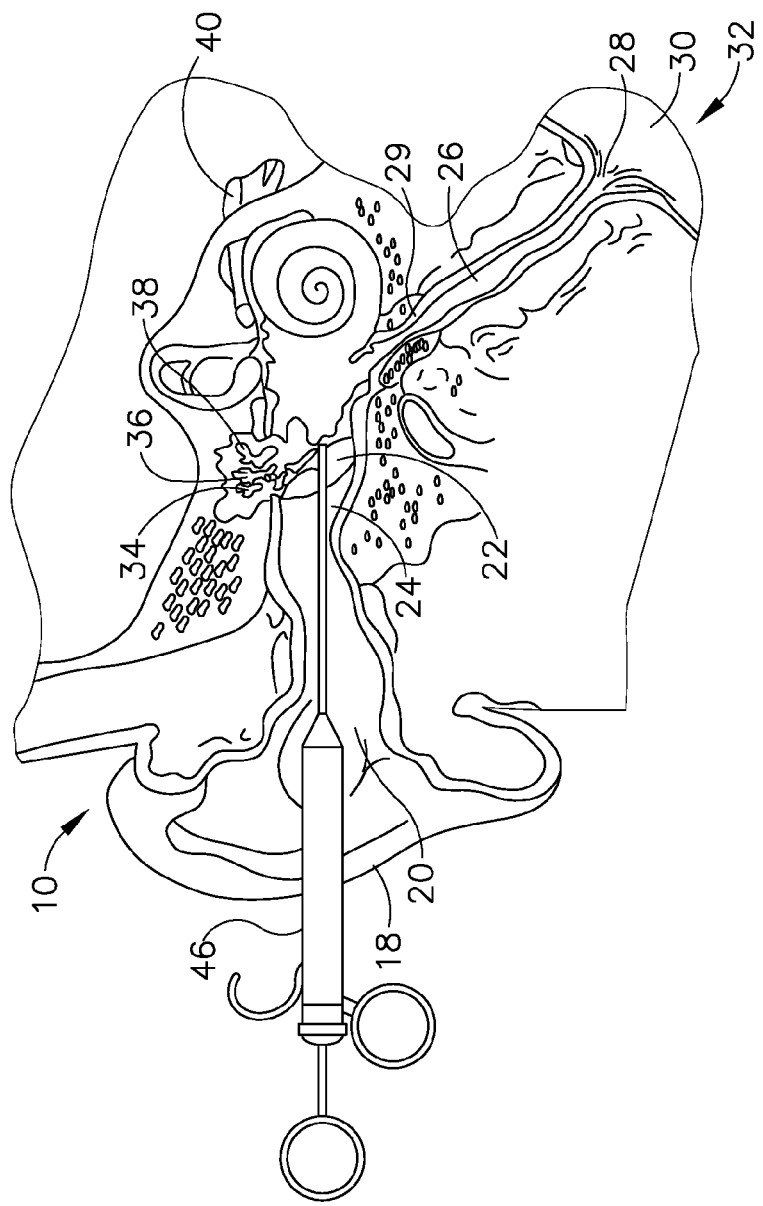
FIG. 4 depicts a cross-sectional view of the ear of FIG. 1, with a syringe perforating an eardrum.

FIG. 4 shows an exemplary alternative method of relieving middle ear (14) pressure. As can be seen, a hypodermic needle (46) is driven through tympanic membrane (22). Hypodermic needle (46) may then be used to manually withdraw fluid from middle ear (14). However, it should be understood that such a procedure shown in FIG. 4 may only result in removal of fluid from the upper portion of Eustachian tube (26). Thus, while effective at removing fluid from middle ear (14), some fluid may still remain when the procedure shown in FIG. 4 is used.

Although the procedures shown in FIGS. 3 and 4 may be effective in treating fluid buildup in middle ear (14), such procedures may be undesirable because both procedures involve a creating a perforation in tympanic membrane (22). Procedures leading to a perforation of tympanic membrane (22) may be undesirable because, in some instances, such a perforation could become permanent. Moreover, although the procedures described above may remove fluid from middle ear (14), the underlying problem of a blocked Eustachian tube (26) may remain.

Figure 5:
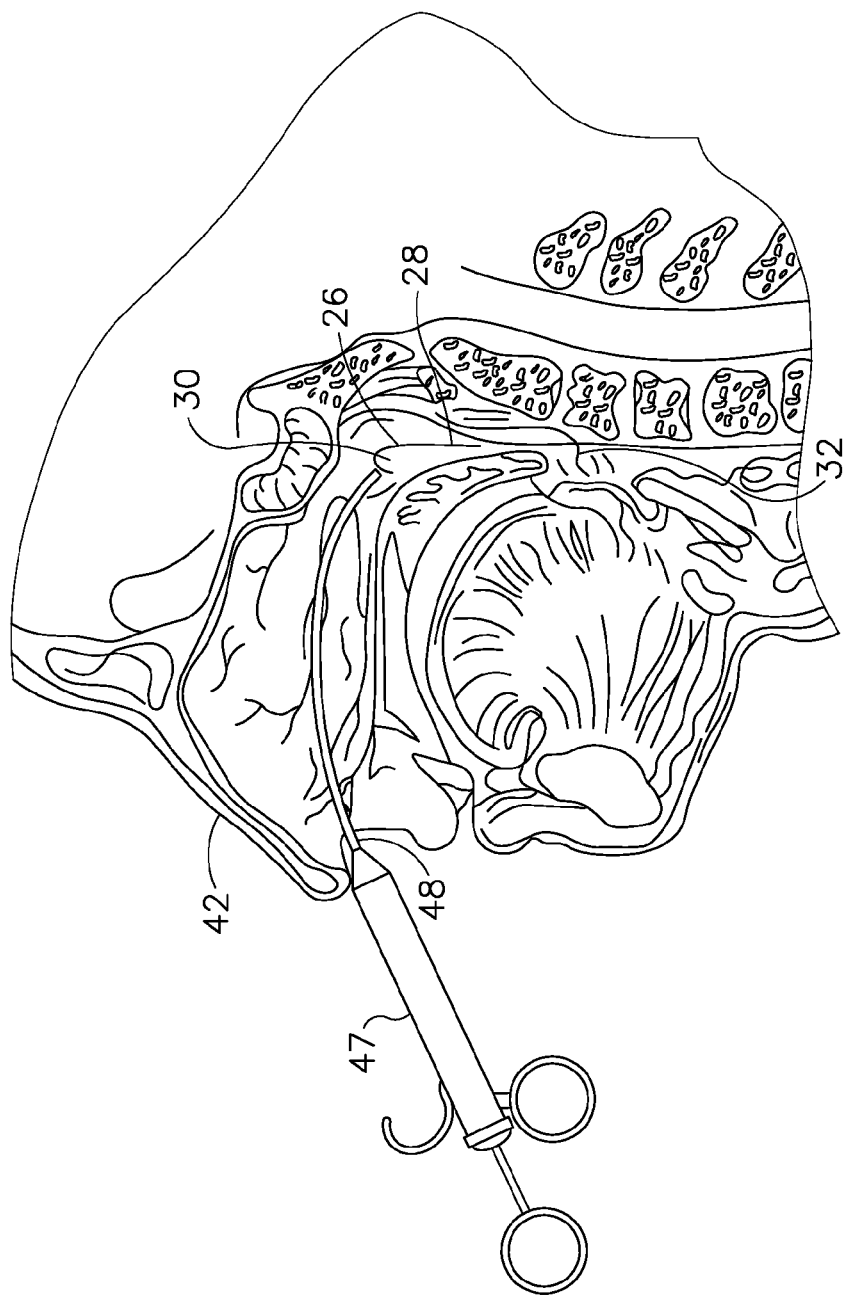
FIG. 5 depicts a cross-sectional view of the head of FIG. 2, with a syringe extending into the nasopharynx and abutting an ostium of the Eustachian tube.
Figure 6:
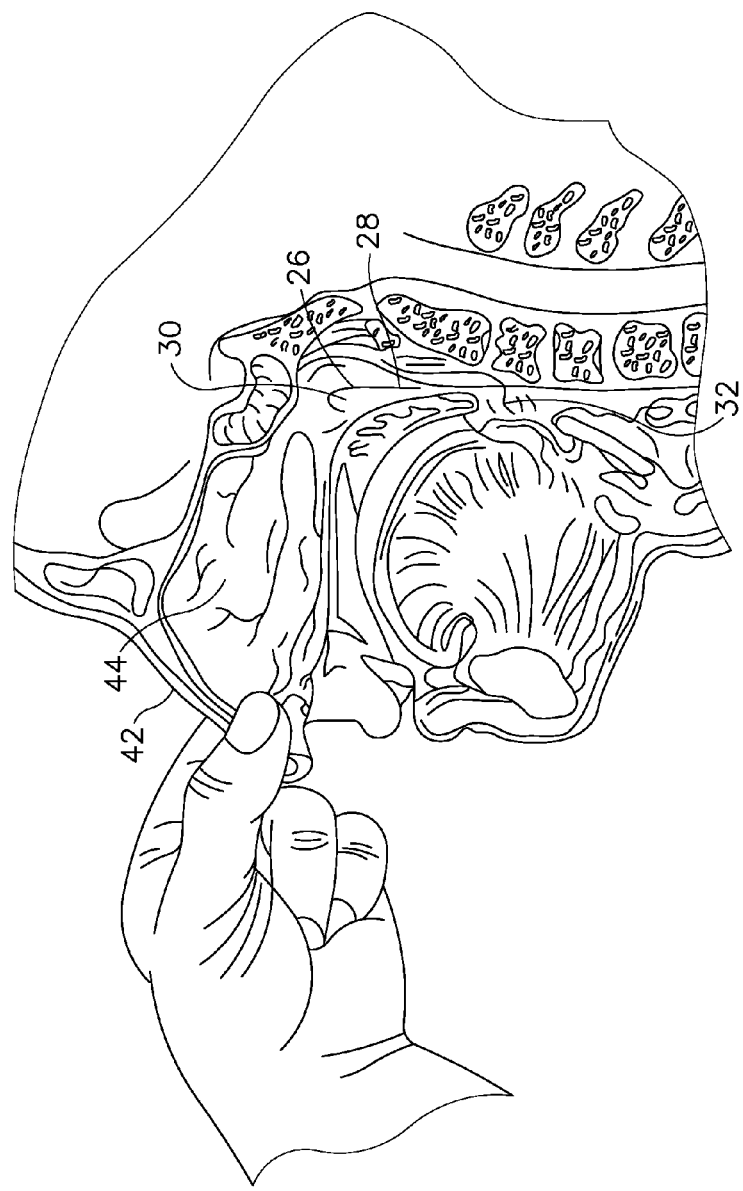
FIG. 6 depicts a cross-sectional view of the head of FIG. 2, with the nasalpharynx being manually plugged.

Another exemplary alternative procedure for treating fluid buildup in middle ear (14) is shown in FIGS. 5 and 6. As can best be seen in FIG. 5, a hypodermic syringe (47) with a flexible tip (48) is shown as being inserted into a nostril to position flexible tip (48) adjacent to ostium (28) of Eustachian tube (26) within nasopharynx (30). Syringe (47) may then be used to inject air or fluid through flexible tip (48) and into Eustachian tube (26). The force of the air traveling into Eustachian tube (26) may relieve congestion and reestablish middle ear (14) ventilation. In some circumstances this procedure may be referred to as politzerization. As shown in FIG. 6, such a procedure may optionally be performed while the nostrils are pinched shut with the patient simultaneously swallowing. Such a technique may aid in forcing air into Eustachian tube (26). While the procedure described above may be effective at opening Eustachian tube (26), it should be understood that the procedure does not necessarily clear fluid away from middle ear (14).

While not shown, it should be understood that a similar procedure to the politzerization procedure described above may be performed. Such a procedure may be referred to as a "valsalva" maneuver and may be accomplished by the patient forcibly blowing air into middle ear (14) while holding the nostrils closed. Such a procedure may also be colloquially referred to as "popping" the ear. While this procedure may open Eustachian tube (26), it should be understood that it may not necessarily lead to fluid being cleared from middle ear (14). Further procedures for treatment of fluid buildup in middle ear (14) are described in Ser. No. 14/317,269; and U.S. Pat. Pub. No. 2010/0274188, which are incorporated by reference herein.

II. Overview of Exemplary Eustachian Tube Dilation Systems

In some instances it may be desirable to dilate at least a portion of a Eustachian tube (26). For instance, as described above, in some circumstances a Eustachian tube (26) may become blocked or otherwise inflamed such that natural draining and ventilation of the middle ear (14) does not occur. In such circumstances, fluid buildup in the middle ear (14) may occur thus leading to chronic infection. While symptoms caused by such a blockage of the Eustachian tube (26) may be treated using procedures described above, treatment of the condition itself may still be desired. One such treatment may include the dilation of the Eustachian tube (26), thereby opening the Eustachian tube (26) to drain fluid from the middle ear (14) and restore natural functioning of the Eustachian tube (26).

The various examples described herein may dilate the Eustachian tube (26) through the use of a balloon catheter or other working instrument. By way of example only, a guide catheter may be inserted through a nostril of a patient and into the nasopharynx (30) to a position adjacent to the ostium (28) of the Eustachian tube (26). The balloon catheter may then be advanced relative to the guide catheter with the guide catheter directing the balloon catheter into the ostium (28) of the Eustachian tube (26). The balloon catheter may then be directed through the Eustachian tube (26) to a position where the balloon catheter may be expanded to dilate the Eustachian tube (26). Exemplary components that may be used to perform such a procedure are described in greater detail below.

A. Exemplary Guide Catheter

FIG. 7A shows an exemplary guide catheter (100) that may be used in a procedure to dilate a Eustachian tube (26) or other natural anatomical passageway. As can be seen, guide catheter (100) comprises an elongate tubular shaft (102) including a proximal end (104) and a distal end (106) and a lumen (108) extending therebetween. It should be understood that guide catheter (100) may have any suitable length, diameter, angle of bend, and location of bend along the length of catheter (100), to facilitate accessing the ostium (28) of the Eustachian tube (26). By way of example only, in some examples guide catheter (100) may have a length between about 8 cm and about 20 cm. In other examples, guide catheter (100) may have a length between about 10 cm and about 15 cm. In still other examples, guide catheter (100) may have a length of about 11 cm. Of course, any other suitable dimensions may be used.

FIG. 7B shows a cross-section of tubular shaft (102). As can be seen, shaft (102) has an outer shaft tube (110), an inner shaft tube (112) and a lumen (108). Outer shaft tube (110) may be constructed of a stiff material such as stainless steel, nitinol, hard plastic, etc Inner tube shaft (112) may be constructed of a relatively more flexible material such as a polymeric material including but not limited to nylon. In some examples, inner shaft tube (112) may further include a PTFE liner. Lumen (108) is generally configured such that a balloon dilation catheter (200), described below, may be slidably disposed within lumen (108). Lumen (108) of the present example has a diameter of between about 2 mm and 3 mm. In other examples, lumen (108) may have a diameter of between 2.5 mm and 2.6 mm. Again, any other suitable dimensions may be used. In the present example, the combination of guide catheter (100) and balloon catheter (200) form a compact system that is configured for one-handed operation.

FIG. 8 shows a detailed view of distal portion (120) of guide catheter (100). Distal portion (120) of the present example includes a bend (122) with an angle between about 45 degrees and about 65 degrees. In other examples, bend (122) may range between about 50 degrees and 60 degrees. In still other examples, bend (122) may be about 55 degrees. Alternatively, any other suitable bend angle may be used. Regardless of the particular bend angle of bend (122) it should be understood that bend (122) is configured to facilitate access into a Eustachian tube (26) from the nasopharynx (30) of a patient, as will be described in greater detail below.

Distal portion (120) of guide catheter (100) further includes a distal tip (124). Distal tip (124) comprises a transparent material such as a polymer including, but not limited to, nylon, polyether block amides (e.g., PEBAX® by Arkema), and/or PTFE. As will be understood, the transparent nature of distal tip (124) may permit dilation catheter (200) to be visible through distal tip (124). In addition to distal tip (124) being comprised of a transparent material, such a material may also be configured to be more flexible relative to the material of elongate shaft (102) such that distal tip (124) is atraumatic in character. In other examples, distal tip (124) may be infused with 20% barium sulfate or other similar radiopaque materials, thereby making distal tip (124) visible under x-ray or other radiographic visualization. Other suitable materials that may be used to form distal tip (124) (or that may be otherwise incorporated into distal tip (124)) will be apparent to those of ordinary skill in the art in view of the teachings herein.

Referring again to FIG. 7A, a proximal portion (130) of guide catheter (100) includes a proximal hub (132) to aid in insertion of balloon dilation catheter (200) into the Eustachian Tube (26). Hub (132) has a larger diameter proximal end (134) and a smaller diameter middle section (136) to facilitate stabilization of guide catheter (100) in the nose (42), rotation of guide catheter (100) and insertion of balloon dilation catheter (200) as will be described in further detail below. Hub (132) is ergonomically designed for insertion, location and rotation with slight manipulations with one hand.

B. Exemplary Dilation Catheter

FIG. 9A shows dilation catheter (200), which is generally insertable into lumen (108) of guide catheter (100) for dilation of a Eustachian tube (26). Dilation catheter (200) comprises an elongate shaft (202) having a proximal end (214) and a distal end (218). Dilation catheter (200) further includes a balloon (204) located proximal to a distal tip (212) of distal end (218). Balloon (204) comprises a polymer balloon and may be compliant, semi-compliant, or non-compliant. In some examples, balloon (204) may comprise a suitable non-compliant material such as polyethylene terepthalate (PET), PEBAX®, nylon, or the like. Balloon (204) may be of any diameter suitable to dilate a Eustachian tube (26). For instance, in some examples balloon (204) may be of an inflated diameter ranging between about 2 mm to about 8 mm. In other examples, the inflated diameter of balloon (204) may range between about 5 mm and 6 mm. Alternatively, any other suitable diameters may be provided. Balloon (204) may also be of any suitable working length. For instance, in some examples balloon (204) may have a working length between about 12 mm and 24 mm. Balloon (204) may comprise any suitable combination of diameter and working length, as will be apparent to those of ordinary skill in the art in view of the teachings herein. Some merely exemplary combinations may include, for example, 2 mm×12 mm, 3.5 mm×12 mm, 5 mm×16 mm, 5 mm×24 mm, 6 mm×16 mm, 6 mm×20, 6 mm×24 mm, 7 mm×16 mm, and 7 mm×24 mm.

Balloon (204) may be expanded to dilate the Eustachian tube (26) after it is placed in a desired location therein. For example, the Eustachian tube (26) includes a pharyngeal ostium (28), and dilation catheter (200) may be advanced to position balloon (204) in the pharyngeal ostium (28). An endoscope may be used to assist in positioning balloon dilation catheter (200). The endoscope may be advanced through the nasal passage to view dilation catheter (200). A marker (208) on elongate shaft (202) of dilation catheter (200) can be viewed from the endoscope to approximate a location of balloon (204) relative to the opening of the Eustachian tube (26) based on a distance of marker (208) from a proximal end of balloon (204). Accordingly, dilation catheter (200) can be moved to place marker (208) in a desired location before expansion of balloon (204) in the Eustachian tube (26). Although only marker (208) is shown, it should be understood that in other examples dilation catheter (200) may include any suitable number of markers positioned at various locations along the length of dilation catheter (200).

Dilation catheter (200) further includes an actuator (210). Actuator (210) has a proximal side (220) and a distal side (222). In the present example, actuator (210) is secured to elongate shaft (202) of dilation catheter (200) by adhesive bonding, although any other suitable means of securing actuator (210) may be used. Actuator (210) is configured to allow for single-handed manipulation of dilation catheter (200). Although actuator (210) may be used in any suitable way, in one merely exemplary use actuator (210) is gripped with a thumb and index finger of an operator while any remaining fingers of the operator may be free to grip the endoscope or any other instrument. Actuator (210) thus allows for easy, ergonomic one-handed advancement of balloon dilation catheter (200) through guide catheter (100) and into the Eustachian Tube (26).

Elongate shaft (202) comprises a proximal portion (238) that is proximal to actuator (210). Elongate shaft (202) further comprises a first distal portion (240) and a second distal portion (250) that are distal to actuator (210). First distal portion (240) is sufficiently stiff to be guided through the nasal cavity and into the Eustachian Tube (26) and is constructed of stainless steel (or other biocompatible material) and preferably includes a stainless steel hypotube. Proximal portion (238) and second distal portion (250), on the other hand, are relatively flexible and are simply constructed of a polymeric material including but not limited to PEBAX® that extends through the length of elongate shaft (202). While first distal portion (240) is of a stiffness such that actuator (210) may guide dilation catheter (200) though a nasal cavity and into a Eustachian tube (26), second distal portion (250) is sufficiently flexible to permit balloon (204) to flex into position as dilation catheter (200) is advanced through a nasal cavity and into a Eustachian tube (26). Proximal portion (238) is similarly flexible such that elongate shaft (202) will not interfere with the endoscope as actuator (210) is used to advance dilation catheter (200).

FIG. 9B shows a cross-section of shaft (202). As can be seen, shaft (202) comprises an inflation lumen (232), and a working lumen (234). Inflation lumen (232) is in communication with the interior of balloon (204) distally, and an inflation port (230) proximally. Accordingly, inflation lumen (232) provides a passage for fluid communication to balloon (204) such that balloon (204) may be inflated by connecting an inflation device (not shown) to inflation port (230) to thereby inject fluid into balloon (204).

Working lumen (234) extends longitudinally through shaft (202) from distal (218) end to proximal end (214). Working lumen (234) is configured to receive various other instruments such a guide wire that may be optionally used in conjunction with dilation catheter (200). Additionally, working lumen (234) provides the function of relieving pressure from a Eustachian tube (26) as it is being dilated. In particular, because balloon (204) blocks the Eustachian tube (26) and the opposite end of the Eustachian tube (26) is sealed by the tympanic membrane (22), pressure may potentially build in the space between balloon (204) and the tympanic membrane (22). However, because working lumen (234) extends through shaft (202) and out of the distal end of shaft (202), working lumen (234) provides ventilation of the space between balloon (204) and the tympanic membrane (22), thereby preventing any potential pressure buildup, particularly when balloon (204) is expanded and occupies volume that had previously been occupied by air in the Eustachian tube (26).

As can best be seen in FIG. 10, distal end (218) of dilation catheter (200) further includes a tip (212) and a flexible shaft portion (250). Tip (212) and flexible shaft portion (250) are constructed of a polymeric material including but not limited to PEBAX®. In the present example, PEBAX® extends from the distal end of elongate shaft (202) to the proximal end of balloon (204). Tip (212) of the present example is bulbous in shape to thereby provide atraumatic properties. By way of example only, tip (212) is about 1.5 mm to about 2 mm in length with a maximum outer diameter of between about 2 mm and 3 mm. It should be understood that the shape of tip (212), including its smoothness and roundness, is configured to facilitate advancement of dilation catheter (200) by allowing the distal end of dilation catheter (200) to glide smoothly through a Eustachian tube (26). It should further be understood that tip (212) also acts as a safety stop. For instance, an isthmus (29) of a Eustachian tube (26) is generally about 1 mm in diameter. However, as described above, tip (212) is generally larger in diameter than 1 mm. Accordingly, tip (212) is sized to prevent dilation catheter (200) from passing through the isthmus (29) and into the middle ear (14).

C. Exemplary Use of Exemplary Guide Catheter and Dilation Catheter Assembly

In an exemplary use, guide catheter (100) may be initially advanced into a nostril and through a nasal cavity to a position distal end (106) of guide catheter (100) at, or near the ostium (28) of the Eustachian tube (26). In one embodiment, guide catheter (100) may be passed through a nostril to a Eustachian tube (26) on the ipsilateral (same side) of a head. Alternatively, guide catheter (100) may be passed through a nostril to a Eustachian tube (26) on the contralateral (opposite side) of a head. It should be understood that although guide catheter (100) is described as being used to access a Eustachian tube (26), in other examples a guiding element such as a guidewire or illuminating fiber may be used to assist with the positioning of guide catheter (100).

After guide catheter (100) is in a desired position, dilation catheter (200) is advanced relative to guide catheter (100). In the present example, dilation catheter (200) is advanced through guide catheter (100), although it should be understood that in other examples, dilation catheter (200) may instead be advanced over guide catheter (100). Regardless, dilation catheter (200) is advanced distally of guide catheter (100) to position balloon (204) of dilation catheter (200) within a Eustachian tube (26). To advance and position dilation catheter (200) an operator may place a thumb on proximal side (220) of actuator (210) or within both sides (220, 222) of actuator (210). The thumb may be used to slide dilation catheter (200) through guide catheter (100). Alternatively, the operator may grasp proximal hub (132) of guide catheter (100) and use an index finger placed on proximal side (220) of actuator (210) or in between distal side (222) and proximal side (220) of actuator (210) to advance dilation catheter (200). As dilation catheter (200) is advanced, the larger diameter tip (212) prevents dilation catheter (200) from advancing too far through Eustachian tube (26), as described above. Further, distal side (222) of actuator (210) will contact proximal end (104) of guide catheter (100), such that dilation catheter (200) is only permitted to advance a certain maximum distance relative to guide catheter (100). Accordingly, actuator (210) also may prevent dilation catheter (200) from being advanced too far into a Eustachian tube (26).

Once dilation catheter (200) is positioned at a desired position within a Eustachian tube (26), balloon (204) may be inflated and held in location while in an expanded state for an extended period of time (e.g. several seconds or minutes). Dilation catheter (200) may also deliver a substance to the Eustachian tube (26), such as one or more of the therapeutic or diagnostic agents described herein. Balloon (204) may also carry an expandable stent for delivery into the Eustachian tube (26) upon expansion of balloon (204). Dilation catheter (200) and guide catheter (100) may be removed from the patient after balloon (204) has been deflated/unexpanded. The Eustachian tube (26) will resume functioning, normally opening and closing to equalize atmospheric pressure in the middle ear and protect the middle ear from unwanted pressure fluctuations and loud sounds.

In an alternative use, dilation catheter (200) may be advanced into a nostril of a patent with guide catheter (100) omitted. In such a use, dilation catheter (200) may be used with or without a guide device such as a guide wire or illuminating fiber. Regardless, an operator may advance dilation catheter (200) though a nostril of a patient until proximal side (220) of actuator (210) is adjacent to the patient's nostril. Distal side (222) of actuator (210) will contact patient's nostril, thereby preventing further advancement of dilation catheter (200). Thus even when dilation catheter (200) is used without guide catheter (100), actuator (210) may prevent dilation catheter (200) from being advanced too far within a Eustachian tube (26).

Working lumen (234) permits the optional injection of water, medicament, or even the introduction of a guidewire through injection port (236) at proximal end (216) of proximal connector (206). In order to ensure that inflation port (230) is used for balloon inflation only, inflation port (230) and injection port (236) may optionally comprise different type connectors. For example, inflation port (230) may comprise a female connector whereas injection port (236) comprises a male connector or vice versa. Alternatively, injection port (236) may comprise a right-handed thread connected and inflation port (230) may comprise a left-handed thread connector or vice versa. It may be desirable to inject solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), a surfactant, an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like.

Some nonlimiting examples of antimicrobial agents that may be used include acyclovir, amantadine, aminoglycosides (e.g., amikacin, gentamicin and tobramycin), amoxicillin, amoxicillinlclavulanate, amphotericin B, ampicillin, ampicillinlsulbactam, atovaquone, azithromycin, cefazolin, cefepime, cefotaxime, cefotetan, cefpodoxime, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscamet, ganciclovir, atifloxacin, imipenemlcilastatin, isoniazid, itraconazole, ketoconazole, metronidazole, nafcillin, nafcillin, nystatin, penicillin, penicillin G, pentamidine, piperacillinitazobactam, rifampin, quinupristindalfopristin, ticarcillinlclavulanate, trimethoprimlsulfamethoxazole, valacyclovir, vancomycin, mafenide, silver sulfadiazine, mupirocin (e.g., Bactroban, Glaxo SmithKline, Research Triangle Park, N.C.), nystatin, triamcinolonelnystatin, clotrimazolelbetamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acid form); non-pathogenic or "friendly" microbes that cause the production of hydrogen peroxide or other substances that kill or inhibit the growth of pathogenic microbes (e.g., *lactobacillus*); antimicrobial proteins or peptides such as those described in U.S. Pat. No. 6,716,813, entitled "Use of Antimicrobial Proteins and Peptides for the Treatment of Otitis Media and Paranasal Sinusitis," issued Apr. 6, 2004, the disclosure of which is incorporated by reference herein, or antimicrobial metals (e.g., colloidal silver).

Additionally or alternatively, in some applications where it is desired to treat or prevent inflammation the substances delivered may include various steroids or other anti-inflammatory agents (e.g., nonsteroidal anti-inflammatory agents or NSAIDS), analgesic agents or antipyretic agents. For example, corticosteroids that have previously administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexarnethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as mmesulide).

Additionally or alternatively, in some applications, such as those where it is desired to treat or prevent an allergic or immune response and/or cellular proliferation, the substances delivered may include: various cytokine inhibitors such as humanized anti-cytokine antibodies, anti-cytokine receptor antibodies, recombinant (new cell resulting from genetic recombination) antagonists, or soluble receptors; various leucotriene modifiers such as zafirlukast, montelukast and zileuton; immunoglobulin E (IgE) inhibitors such as Omalizumab (an anti-IgE monoclonal antibody formerly called rhu Mab-E25) and secretory leukocyte protease inhibitor); and SYK Kinase inhibitors such as an agent designated as "R-112" manufactured by Rigel Pharmaceuticals, Inc, South San Francisco, Calif.

Additionally or alternatively, in some applications, such as those where it is desired to shrink mucosal tissue, cause decongestion, or effect hemostasis, the substances delivered may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered may include various mucolytics or other agents that modify the viscosity or consistency of mucous or mucoid secretions, including but not limited to acetylcysteine. In one particular embodiment, the substance delivered may comprise a combination of an anti-inflammatory agent (e.g. a steroid or an NSAID) and a mucolytic agent.

Additionally or alternatively, in some applications such as those where it is desired to prevent or deter histamine release, the substances delivered may include various mast cell stabilizers or drugs which prevent the release of histamine such as cromolyn (e.g., Nasal Chroma) and nedocromil.

Additionally or alternatively, in some applications such as those where it is desired to prevent or inhibit the effect of histamine, the substances delivered may include various antihistamines such as azelastine (e.g., Astylin) diphenhydramine, loratidine, etc.

Additionally or alternatively, in some embodiments such as those where it is desired to dissolve, degrade, cut, break or remodel bone or cartilage, the substances delivered may include substances that weaken or modify bone and/or cartilage to facilitate other procedures wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsinlLEDTA, hyaluronidase, and tosyllysylchloromethane (TLCM).

Additionally or alternatively, in some applications such as those wherein it is desired to treat a tumor or cancerous lesion, the substances delivered may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other antitumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, 1MC-IC11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmetteguerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

In some instances, a local anesthetic, such as Lidocaine is injected through working lumen (234) prior to dilation of the Eustachian tube (26). Working lumen (234) can be used for venting during dilation so that pressure in the middle ear (14) does not increase or decrease.

D. Exemplary Alternative Guide Catheter

Figure 11:
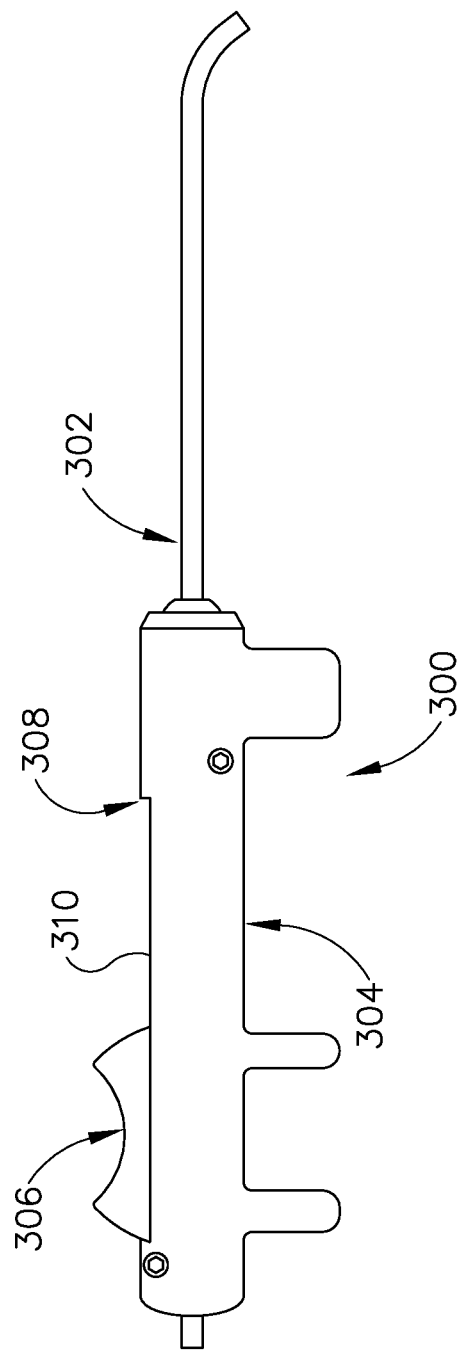
FIG. 11 depicts a side elevational view of an exemplary alternative guide catheter.

FIG. 11 shows an exemplary alternative guide catheter (300), which may be used in lieu of guide catheter (100) described above. Guide catheter (300) is substantially the same as guide catheter (100), except as where otherwise noted herein. Guide catheter (300) of the present example comprises an elongate shaft (302), which is substantially the same as shaft (102) described above. Guide catheter (300) further comprises a handle (304), which is similar in function to proximal hub (130) of guide catheter (100). Handle (304), unlike proximal hub (130), comprises an actuator (306) that may be attached to dilation catheter (200) such that actuator (306) may be used to advance dilation catheter (200). As can be seen, handle (304) includes an elongate track (310), which slidably supports actuator (306), thereby permitting actuator (306) to slide longitudinally relative to handle (304) to thereby advance and retract dilation catheter (200) relative to guide catheter (300). Track (310) further includes a stop (308), which may prevent over insertion of dilation catheter (200) into a Eustachian tube (26).

In an exemplary use of guide catheter (300), guide catheter (300) is gripped by an operator using a handle (304) and shaft (302) is inserted into a nostril of a patient. Because actuator (306) of guide catheter (300) may be attached to dilation catheter (200), it should be understood that as guide catheter (300) is inserted into the nostril, dilation catheter (200) may likewise be inserted into the nostril. However, dilation catheter (200) may remain within shaft (302) until an operator desires to advance dilation catheter (200).

Guide catheter (300) may be advanced within a nostril of the patient until the distal end of shaft is adjacent to an ostium (28) of a Eustachian tube (26). At such a point, an operator may begin advancing dilation catheter (200) separately from guide catheter (300). To engage in such advancement, the operator may slide actuator (306) along track (310). Actuator (306) may be advanced until either dilation catheter (200) is advanced to a desired position or until actuator (306) reaches stop (308). Regardless, once dilation catheter (200) is positioned at a desired position in a Eustachian tube (26), the operator may expand balloon (204) of dilation catheter (200) to dilate the Eustachian tube (26) similarly as described above.

III. Exemplary Eustachian Tube Dilation Systems with Integral Camera

In some instances it may be desirable to include optical sensors and/or light emitters in a dilation catheter similar to catheter (200) described above. For instance, in some patients the particular autonomy of the patient may make maneuvering an endoscope and a guide catheter together within the nostril of the patient challenging. Thus there may be a need for dilation catheters that can provide visualization, guidance, and dilation without requiring a separate endoscope. In other instances, a patient's anatomy may permit use of an endoscope and a guide catheter simultaneously, yet the field of view of the endoscope may be limited by the patient's anatomy or the instruments themselves. Accordingly, the instruments described below include one or more integral optical sensors and/or light emitting features. It should be understood that while the instruments described below are discussed in the context of being usable with each other, each individual instrument may instead be used in conjunction with any instruments described above in addition to, or in lieu of similar instruments.

A. Exemplary Guide Catheter Dilation Catheter Alignment Feature

Figure 12:
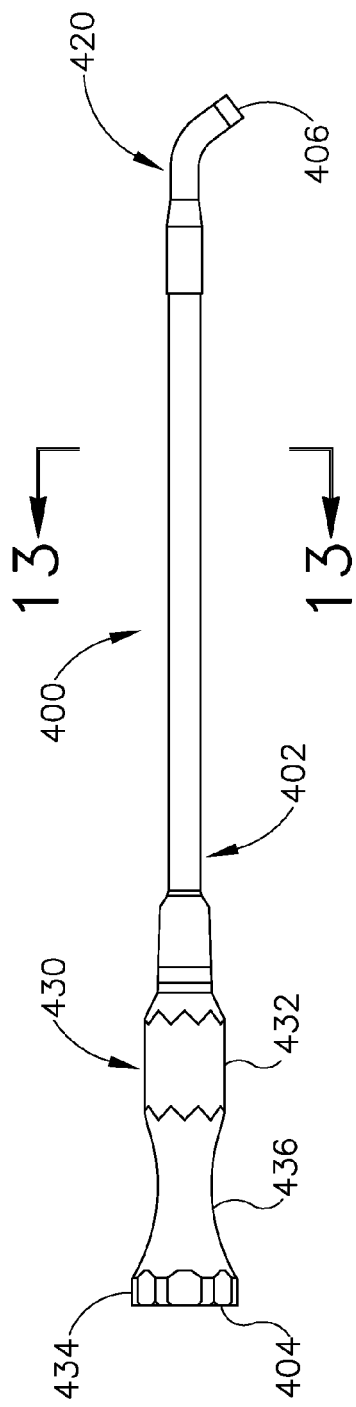
FIG. 12 depicts side elevational view of another exemplary alternative guide catheter.

FIG. 12 shows an exemplary guide catheter (400) that may be used in a procedure to dilate a Eustachian tube (26) or other passageway. Guide catheter (400) is substantially the same as guide catheter (100) described above, expect as otherwise noted herein. For instance, guide catheter (400) comprises an elongate tubular shaft (402) including a proximal end (404) and a distal end (406) and a lumen (408) extending therebetween. It should be understood that, like guide catheter (100), guide catheter (400) may have any suitable length, diameter, angle of bend, and location of bend along the length of catheter (400), to facilitate accessing the opening (28) of a Eustachian tube (26).

Figure 14:
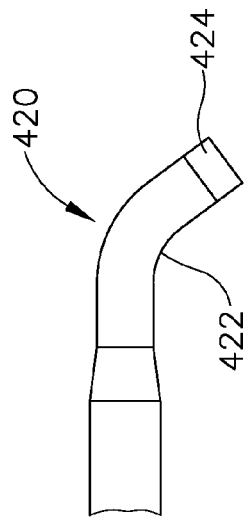
FIG. 14 depicts a detailed side view of the distal end of the guide catheter of FIG. 12.
Figure 13:
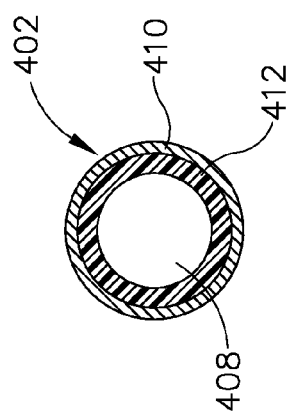
FIG. 13 depicts a cross-sectional view of a shaft of the guide catheter of FIG. 12, taken along line 13-13 of FIG. 12.

FIG. 13 shows a cross-section of tubular shaft (402). As can be seen, shaft (402) has an outer shaft tube (410), an inner shaft tube (412). Outer shaft tube (410) and inner shaft tube (412) are substantially similar to shaft tubes (110, 112) described above such that shaft tubes (410, 412) will not be described in further detail. FIG. 14 shows a detailed view of distal portion (420) of guide catheter (400). Distal portion (420) of the present example includes a bend (422) similar to bend (122) described above. Distal portion (420) of guide catheter (400) further includes a distal tip (424). Distal tip (424), like distal tip (124) described above, comprises a transparent material to permit dilation catheter (200, 500) to be visible through distal tip (424). In addition to distal tip (424) being comprised of a transparent material, such a material may also be configured to be more flexible relative to the material of elongate shaft (402) such that distal tip (424) is atraumatic in character.

Returning to FIG. 12, proximal portion (430) of guide catheter (400) is generally configured to aid in manipulating guide catheter (400) and to aid in inserting dilation catheter (200, 500) into a Eustachian tube (26) using a single hand. Proximal portion (430) includes a proximal hub (432), a proximal end (434), and a middle section (436). Proximal hub (432) is configured to aid in insertion of dilation catheter (200, 500) into the Eustachian tube (26). Proximal end (434) and middle section (436) are configured to facilitate stabilization of guide catheter (400) when guide catheter (400) is inserted into a nose (42).

Figure 15:
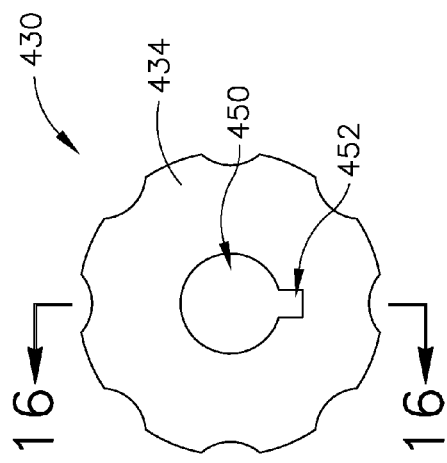
FIG. 15 depicts a rear elevational view of the guide catheter of FIG. 12.
Figure 16:
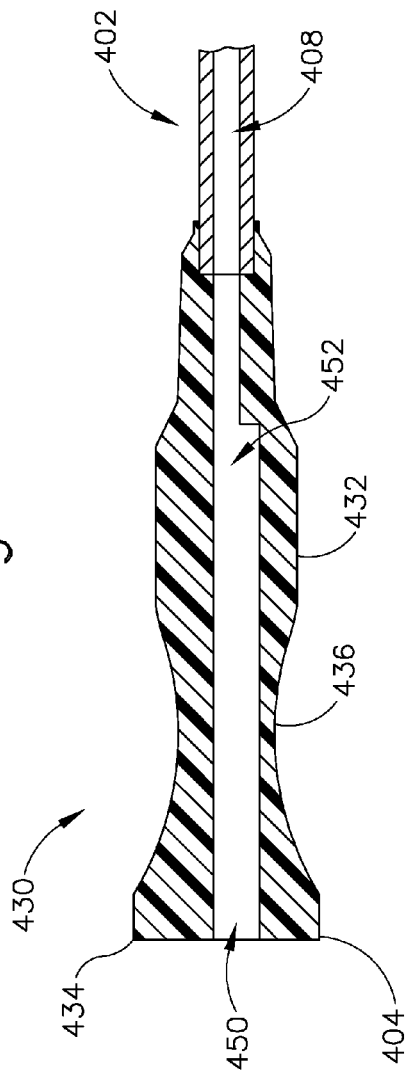
FIG. 16 depicts a detailed cross-sectional view of the guide catheter of FIG. 12, taken along line 16-16 of FIG. 15.

FIGS. 15 and 16 show proximal portion (430) of guide catheter (400) in more detail. In particular, as can be seen in FIG. 15, proximal end (434) of proximal portion (430) includes an opening (450) that is in communication with lumen (408) described above. Opening (450) of the present example is generally circular in shape and includes a keyway (452) on one side. As will be described in greater detail below, keyway (452) of the present example is rectangular in shape and is generally configured to receive a corresponding key (526) of dilation catheter (500) to thereby prevent rotational movement of dilation catheter (500) relative to guide catheter (400). As can best be seen in FIG. 16, keyway (452) extends distally from proximal end (434) through proximal portion (430). Keyway (452) extends parallel to lumen (408). The depth of the extension of keyway (452) into proximal portion (430) is shown as corresponding to about three fourths of proximal portion (430). In other examples, keyway (452) may extend into proximal portion (430) any suitable length. It should be understood that a suitable length of extension for keyway (452) may be at least in part determined by the particular extension of key (526) described below. For instance, it may be desirable to for keyway (452) to have an extension at least as long as key (526) to thereby permit complete insertion of dilation catheter (500) into guide catheter (400) as will be described in greater detail below.

Although opening (450) is described herein as including keyway (452), it should be understood that the same functional purpose of keyway (452) could be accomplished using a variety of opening geometries extending proximally into proximal portion (430). For instance, in some examples opening (450) may comprise a triangular shape that is sized at least as large as lumen (408). In such an example, dilation catheter (500) may include a similar corresponding cross-sectional geometry such that the triangular shape of opening (450) may restrict rotational movement of dilation catheter (500) relative to guide catheter (400) when the corresponding geometries engage each other. In still other examples, opening may likewise comprise any other suitable shape such as square, hexagonal, octagonal, elliptical, etc. Furthermore, although opening (450) is shown as comprising a single keyway (452), it should be understood that in yet other examples opening (450) may comprise any other suitable number of keyways (452).

Although various features of guide catheter (400) are described herein, it should be understood that in other examples guide catheter (400) may include various other features. By way of example only, in one merely exemplary version of guide catheter (400) it may be desirable to include imaging sensors, illumination source(s) and/or other visualization features. A guide catheter that may include such features may be provided in accordance with the teachings of U.S. Provisional Patent App. No. 62/140,104, entitled "Guide Catheter with Image Capture and Light Emission Features," filed Mar. 30, 2015, the disclosure of which is incorporated by reference herein.

B. Exemplary Dilation Catheter with Integral Camera and Alignment Feature

Figure 17:
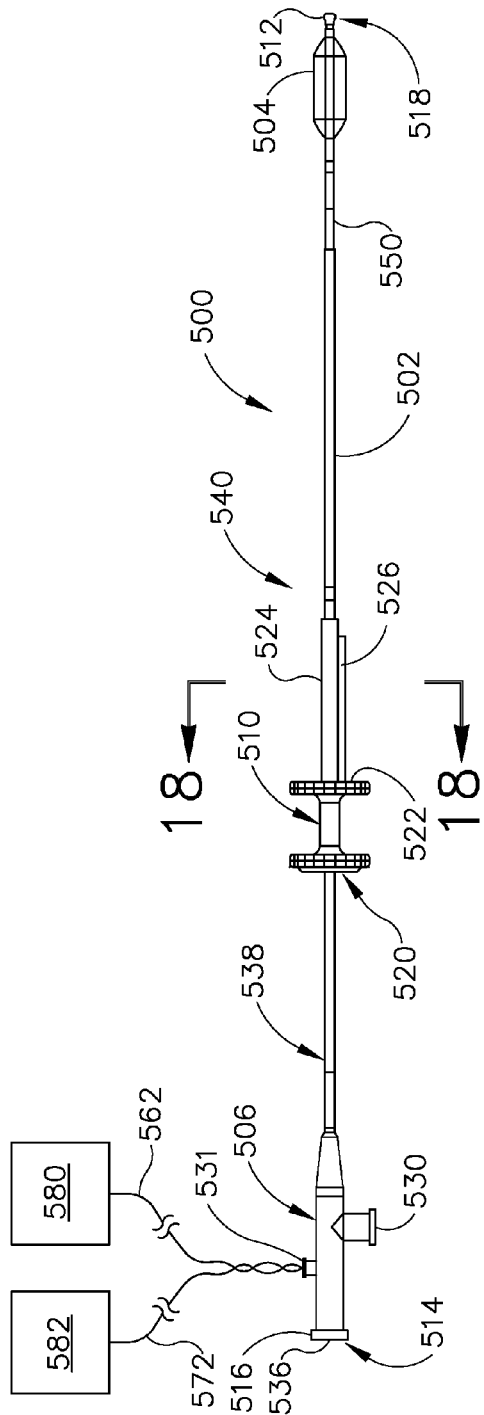
FIG. 17 depicts a side elevational view of an exemplary alternative dilation catheter for use with the guide catheter of FIG. 12.

FIG. 17 shows dilation catheter (500), which is generally insertable into lumen (108) of guide catheter (100) or lumen (408) of guide catheter (400) for dilation of a Eustachian tube (26). Dilation catheter (500) is substantially the same as dilation catheter (200) described above, except where as otherwise noted herein. For instance, dilation catheter (500) comprises an elongate shaft (502) having a proximal end (514) and a distal end (518). Dilation catheter (500) further includes a balloon (504) oriented proximal to a distal tip (512) of distal end (518). In some versions, distal tip (512) has a slightly elliptical cross-sectional profile, with a major diameter of approximately 0.102 inches and a minor diameter of approximately 0.094 inches. Balloon (504) is comprised of a polymeric material and may be compliant, semi-compliant, or non-compliant. Like balloon (204), balloon (504) is generally configured to dilate a Eustachian tube (26) upon being guided to a desired location therein and expanded. By way of example only, balloon (504) may be configured to withstand being inflated at fluid pressures greater than 4 atmospheres, and the components of dilation catheter (500) that are in fluid communication with balloon (504) may be configured to withstand such fluid pressures as well.

Dilation catheter (500) further includes an actuator (510). Actuator (510), like actuator (210) described above, has a proximal side (520) and a distal side (522). Elongate shaft (502) comprises a proximal portion (538) that is proximal to actuator (510). Elongate shaft (502) further comprises a first distal portion (540) and a second distal portion (550) that are distal to actuator (510). The mechanical properties of proximal portion (538), first distal portion (540), and second distal portion (550) are substantially the same as those described above with respect to elongate shaft (202) such that further details will not be described here.

Actuator (510) of the present example further comprises a distal extension member (524). Distal extension member (524) is generally cylindrical in shape and extends distally from distal side (522) of actuator (510). Distal extension member (524) fixedly positioned coaxially about shaft (502), although such a positioning is merely optional and in other examples distal extension member (524) may be offset from a coaxial position relative to shaft (502). Distal extension member (524) includes an integral key (526). Key (526) is configured to engage keyway (452) as described above. Key (526) extends laterally from distal extension member (524). Key (526) of the present example also extends longitudinally along the length of extension member (524) for approximately the length of balloon (504), although this length is merely optional. As will be understood, the length of key (526) of the present example is configured such that key (524) begins engagement with keyway (452) of guide catheter (400) when distal end (518) of dilation catheter (500) reaches the distal end (406) of guide catheter (400). Although key (526) of the present example is shown as having a generally rectangular cross-sectional profile, in other examples key (526) may have any other suitable cross-sectional profile as described above with respect to keyway (452). In the present example, key (526) is unitary with distal extension member (524). In other examples, key (526) may be a separate component that is fixedly secured to distal extension member (524).

Figure 18:
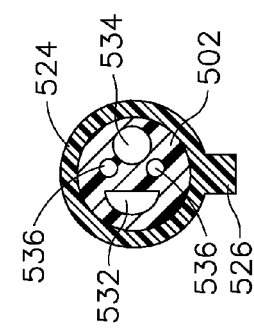
FIG. 18 depicts a cross-sectional view of a shaft of the dilation catheter of FIG. 17, taken along line 18-18 of FIG. 17.

FIG. 18 shows a cross-section of shaft (502). As can be seen, shaft (502) comprises an inflation lumen (532), a working lumen (534), and two access lumens (536). Distal extension member (524) is shown as coaxially surrounding shaft (502). Inflation lumen (532) is in communication with the interior of balloon (504) distally; and an inflation port (530) proximally. Accordingly, inflation lumen (532) provides a passage for fluid communication to and from balloon (504) such that balloon (504) may be inflated by connecting an inflation device (not shown) to inflation port (530) to thereby inject fluid into balloon (504).

Working lumen (534) extends longitudinally through shaft (502) from distal (518) end to proximal end (514). Working lumen (534) is configured to receive various other instruments such a guide wire that may be optionally used in conjunction with dilation catheter (500). Additionally, working lumen (534) provides the function of relieving pressure from a Eustachian tube (26) as it is being dilated. In particular, because balloon (504) blocks the Eustachian tube (26) and the opposite end of the Eustachian tube (26) is sealed by the tympanic membrane (22), pressure may potentially build in the space between balloon (504) and the tympanic membrane (22). However, because working lumen (534) extends through shaft and out of the distal end of shaft (502), working lumen (534) provides ventilation of the space between balloon (504) and the tympanic membrane (22), thereby preventing any potential pressure buildup, particularly when balloon (504) is expanded and occupies volume that had previously been occupied by air in the Eustachian tube (26).

Access lumens (536) extend from distal end (518) of shaft (502) to a wire port (531) positioned on proximal end (514) of shaft (502). Each access lumen (536) is configured to provide a space to thread wires and/or illumination fibers through shaft (502). As will be described in greater detail below, distal end (518) of dilation catheter (500) includes a ball tip (512) that is equipped with an image sensor (560) and one or more light sources (570). Accordingly, access lumens (536) permit wires to be run through shaft (502) from wire port (531) to distal end (518) of shaft (502).

Figure 19:
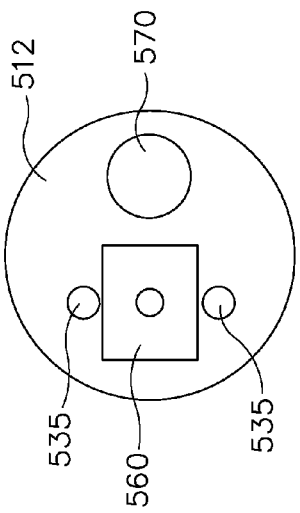
FIG. 19 depicts a front elevational view of the dilation catheter of FIG. 17.
Figure 20:
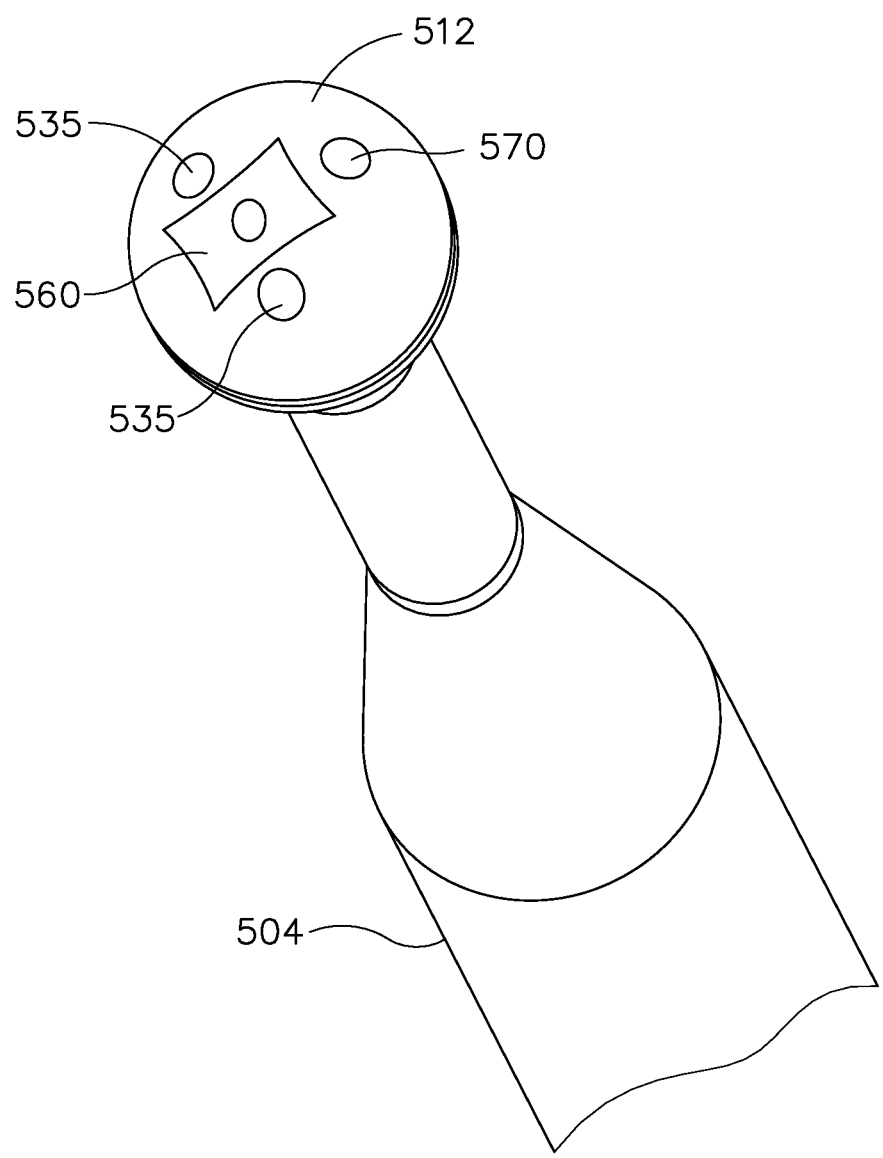
FIG. 20 depicts a perspective view of a ball tip of the dilation catheter of FIG. 17.

As noted above, distal end (518) of dilation catheter (500) further includes ball tip (512) and a flexible shaft portion (550). Ball tip (512) and flexible shaft portion (550) are similar to tip (212) and shaft portion (250) described above, and are constructed of a polymeric material including but not limited to PEBAX®. However, unlike tip (212), ball tip (512) includes an image sensor (560), a light source (570), and a plurality of vent openings (535). As can best be seen in FIGS. 19-20, image sensor (560) is positioned adjacent to vent ports (535), which are coupled to working lumen (534) of shaft (502). In the present example, image sensor (560) is mounted to ball tip (512) via a flexible bonding adhesive, such as Ultra Light-Weld™ flexible catheter bonding adhesive, to enhance the atraumatic nature of ball tip (512). Of course, in other examples image sensor (560) may be secured to ball tip (512) using any other suitable means. While image sensor (560) is shown as being slightly offset from the longitudinal axis of shaft (502), dilation catheter (500) may be readily modified such that image sensor (560) is coaxially aligned with the longitudinal axis of shaft (502) at distal end (518).

Image sensor (560) of the present example is shown schematically. Image sensor (560) may comprise any suitable image sensor such as a micro-complementary metal-oxide semiconductor (CMOS) image sensor. One merely exemplary suitable sensor micro-CMOS image sensor may be the NanEye 1 mm×1 mm image sensor produced by AWAIBA Lba of Funchal, Madeira. It should be understood that image sensor (560) may optionally be equipped with one or more lens elements to magnify, filter, or otherwise adjust light passing into image sensor (560). It should also be understood that one or other optically transmissive features may be positioned distal to image sensor (560) to enhance imaging through image sensor (560) and/or to protect image sensor (560). Image sensor (560) connects to a wire bundle (562), which is threaded through access lumens (536) and out of wire port (531). Wire bundle (562) permits image sensor (560) to connect to an image processing unit (580) which may include, or be connected to, a display. Although image sensor (560) is described herein as being separate from image processing unit (580), it should be understood that in other examples image sensor (560) may include at least some image processing components onboard. In such examples, the image processing unit (580) may be omitted and wire bundle (562) may connect directly to a display.

Light source (570) is generally configured to project light distally from ball tip (512) to illuminate a visualization area that is positioned distal to tip (512). Light source (570) of the present example includes an illumination fiber (572) disposed within ball tip (512). However, it should be understood that light source (570) may comprise any other kind of suitable light emitting feature such as one or more light emitting diodes. In still other examples, a lens may be placed distally of light source (570) to focus, direct, diffuse, or otherwise alter light emitted from light source (570). Furthermore, while only a single light source (570) is shown, it should be understood that other versions of ball tip (512) may include a plurality of light sources (570). By way of example only, illumination fiber (572) may have an outer diameter of approximately 0.009 inches or any other suitable outer diameter. Illumination fiber (572) extends into shaft (502) and is threaded through one or more of access lumens (526) and out of shaft (502) via port (531). Illumination fiber (572) is then attached to a light generator (582) or other similar device. Light generator (582) and illumination fiber (572) may be configured to provide illumination in the visual light spectrum, infrared spectrum, or some other selected bandwidth.

In some exemplary methods of manufacture, tip (512) may be fitted with image sensor (560) and light source (570) by first starting with a dilation catheter like dilation catheter (200). A mandrel may then be forced into the distal opening of tip (212), thereby widening the distal opening. By way of example only, the mandrel may be coated in polytetrafluoroethylene (PTFE) and may have an outer diameter between approximately 0.053 inches and approximately 0.060 inches. Image sensor (560) and light source (570) may be positioned in the opening and may then be bonded in place using flexible bonding adhesive (e.g., Ultra Light-Weld™). Other suitable methods of manufacture will be apparent to those of ordinary skill in the art in view of the teachings herein.

In some instances, image sensor (560) (or some optically transmissive feature that is distal to image sensor (560)) may become covered with mucus and/or other debris making it difficult to obtain satisfactory images from image sensor (560). It may therefore be desirable to include one or more features that are operable to clean away such debris. By way of example only, dilation catheter (500) may include a wiping feature that is configured and operable in accordance with at least some of the teachings of U.S. Pub. No. 2014/0261545, entitled "Apparatus for Wiping Angled Window of Endoscope," published Sep. 18, 2014, the disclosure of which is incorporated by reference herein. As another merely illustrative example, dilation catheter (500) may include a flushing feature that is operable to flush debris away using a cascade of fluid in accordance with at least some of the teachings of U.S. Pub. No. 2014/0261579, entitled "Apparatus for Flushing Angled Window of Endoscope," published Sep. 18, 2014, the disclosure of which is incorporated by reference herein. Other suitable features that may be used to provide cleaning of image sensor (560) (or some optically transmissive feature that is distal to image sensor (560)) will be apparent to those of ordinary skill in the art in view of the teachings herein. More broadly, various other suitable components, features, and configurations that may be incorporated into dilation catheter (500) will be apparent to those of ordinary skill in the art in view of the teachings herein.

Figure 21A:
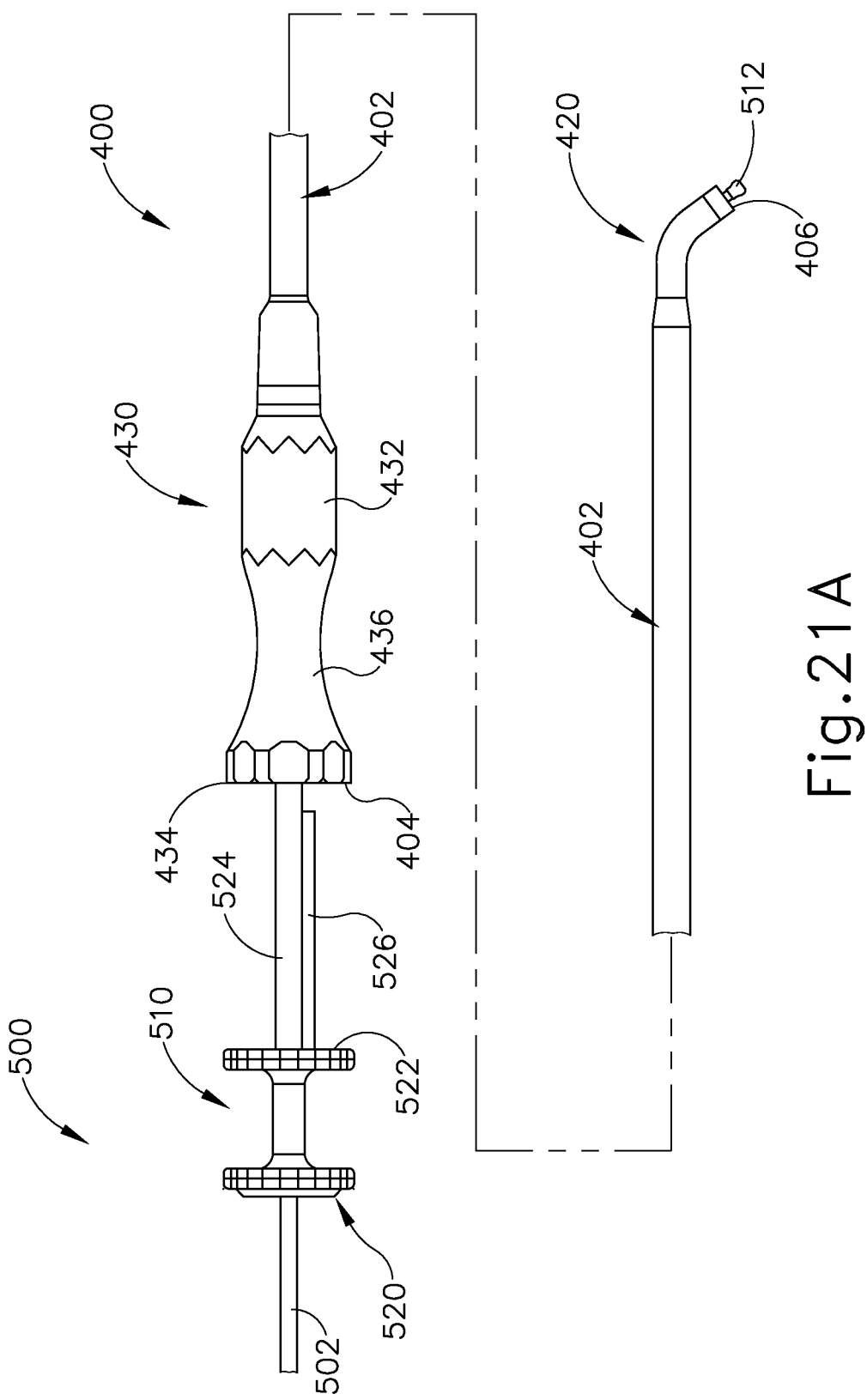
FIG. 21A depicts a side elevational view of the dilation catheter of FIG. 17 partially inserted into the guide catheter of FIG. 12.

C. Exemplary Use of Dilation Catheter with Integral Camera and Alignment Feature Generally guide catheter (400) and dilation catheter (500) may be used in conjunction with each other to dilate a Eustachian tube (26) of a patient. For instance, an operator may initially insert guide catheter (400) into a nostril of a patent. Guide catheter (400) may then be advanced to a position adjacent to an ostium (28) of a Eustachian tube (26). Once guide catheter (400) is positioned, the operator may insert dilation catheter (500) into lumen (408) of guide catheter (400), advancing dilation catheter (500) relative to guide catheter (400). Alternatively, dilation catheter (500) may be pre-inserted in guide catheter (400), as shown in FIG. 21A, when guide catheter (400) is initially inserted into the nostril of the patient. In situations where dilation catheter (500) is pre-inserted in guide catheter (400) when guide catheter (400) is initially inserted into the nostril of the patient, dilation catheter (500) may be positioned relative to guide catheter (400) such that tip (512) of balloon catheter (500) is flush with or just proximal to distal end (406) of guide catheter (400). Key (526) may be inserted into keyway (452) to provide a known and consistent angular orientation of image sensor (560) about the longitudinal axis of catheters (400, 500). It should be understood that image sensor (560) may be used to obtain real-time video imaging at any time during the steps described above, thereby facilitating positioning of distal end (406) and tip (512) near the ostium (28) of the Eustachian tube (26). Light source (570) projects light distally from tip (512), thereby providing illumination for the field of view of image sensor (560).

Figure 21B:
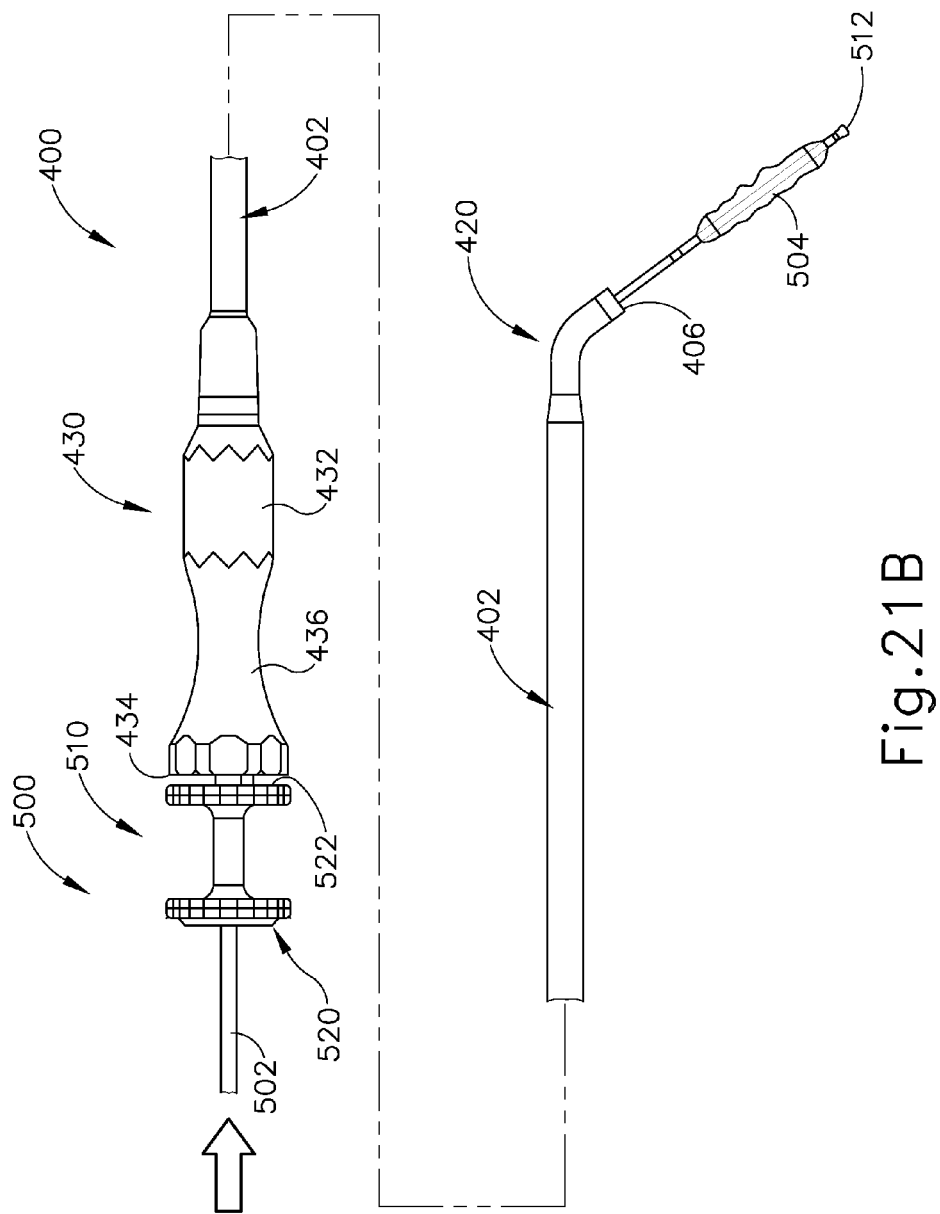
FIG. 21B depicts a side elevational view of the dilation catheter of FIG. 17 fully inserted into the guide catheter of FIG. 12.

Once catheters (400, 500) have reached a point where distal end (406) and tip (512) are sufficiently close to the ostium (28) of the Eustachian tube (26), dilation catheter (500) may be advanced distally relative to guide catheter (400) to drive tip (512) and balloon (504) into the Eustachian tube (26). FIG. 21B shows dilation catheter (500) advanced distally relative to guide catheter (400). Again, key (526) and keyway (452) provide a consistent angular orientation of image sensor (560) about the longitudinal axis of catheters (400, 500) as dilation catheter (500) is advanced. As dilation catheter (500) is advanced from the position shown in FIG. 21A to the position shown in FIG. 21B, balloon (504) is advanced relative to distal end (406) of guide catheter (400). Balloon (504) may be advanced in this way until actuator (510) of dilation catheter (500) is adjacent to proximal end (404) of guide catheter (400), thereby preventing further advancement of dilation catheter (500). It should be understood that in a procedure to dilate a Eustachian tube (26), the position of balloon (504) shown in FIG. 21B may correspond to balloon (504) being positioned within the Eustachian tube (26). Of course in such a procedure, balloon (504) may be located at any position between the position shown in FIG. 21A and the position shown in FIG. 21B. As dilation catheter (400) is being advanced, image sensor (560) may continue to provide real-time video imaging, enabling the operator to observe the condition of the Eustachian tube (26) and the isthmus (29). This may allow the operator to identify a particular location within the Eustachian tube (26) for dilation.

Figure 21C:
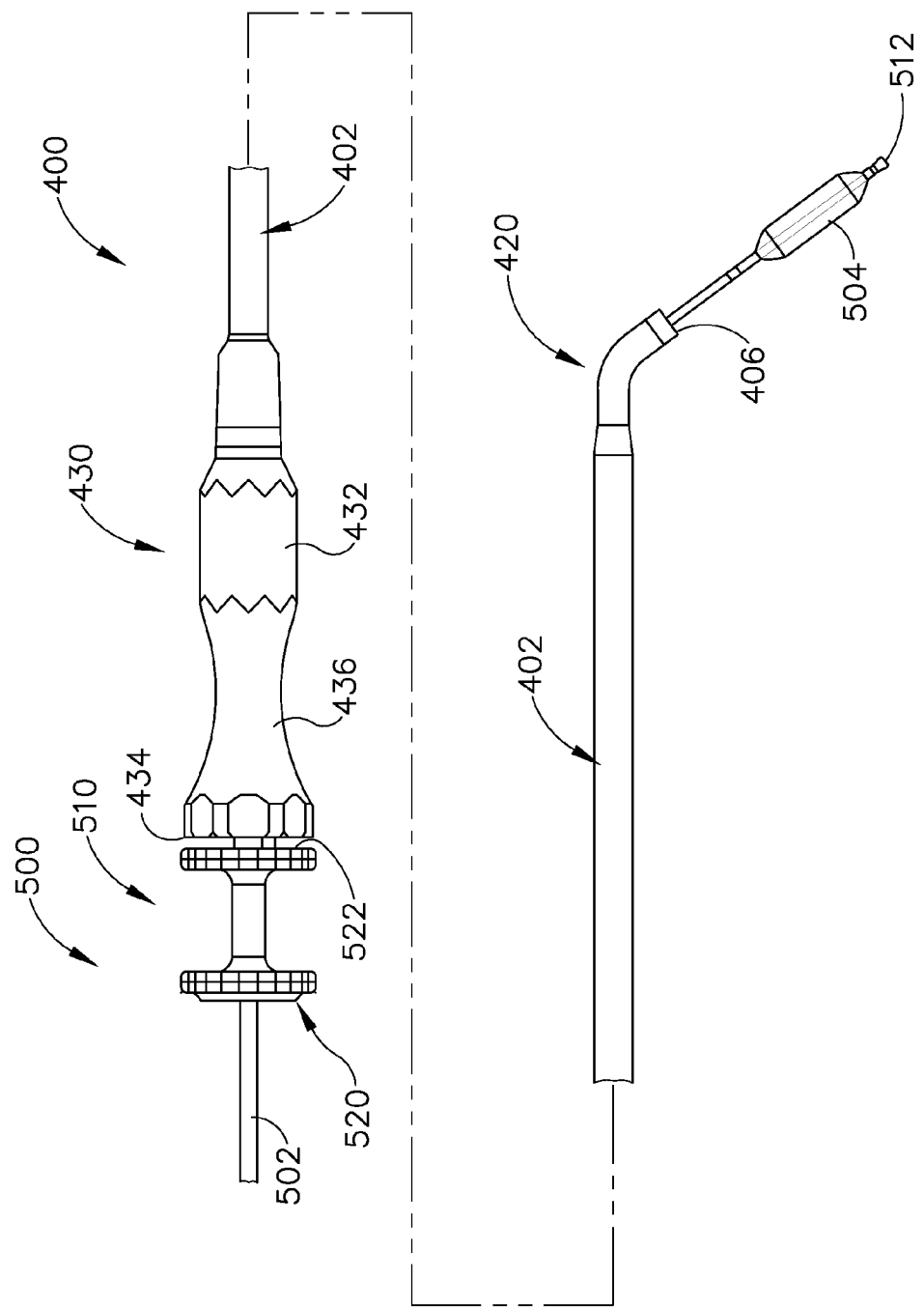
FIG. 21C depicts a side elevational view of the dilation catheter of FIG. 17 fully inserted into the guide catheter of FIG. 12, with a balloon of the dilation catheter in an expanded state.

Once balloon (504) is suitably positioned within the Eustachian tube (26), balloon (504) may be filled to an expanded state to thereby dilate the Eustachian tube (26). FIG. 21C shows balloon (504) in an expanded sate. The operator may maintain balloon (504) in the expanded configuration for any suitable period of time sufficient to complete dilation. The operator may also repeatedly inflate and deflate balloon (504) any suitable number of times. Once the dilation procedure is complete, the operator may retract balloon catheter (500) and guide catheter (400), leaving Eustachian tube (26) dilated. The operator may use image sensor (560) to visualize Eustachian tube (26) before, during, and after the dilation procedure to determine whether the Eustachian tube (26) is sufficiently dilated. Other suitable ways in which balloon catheter (500) and guide catheter (400) may be used will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation catheter system, wherein the dilation catheter system comprises: (a) a guide member, wherein the guide member includes a shaft comprising a distal end and a proximal end, wherein the shaft defines a longitudinal axis; (b) a dilation catheter movable relative to the guide member, wherein the dilation catheter comprises an expandable dilator, wherein the expandable dilator is sized to fit within one or both of a Eustachian tube or a passageway associated with a paranasal sinus; and (c) an image sensor, wherein the image sensor is configured to provide visualization within anatomy of a patient, wherein the image sensor is integral with the dilation catheter.

Example 2

The dilation catheter system of Example 1, wherein the guide member comprises a first alignment feature, wherein the dilation catheter comprises a second alignment feature.

Example 3

The dilation catheter system of Example 2, wherein the first alignment feature of the guide member and the second alignment feature of the dilation catheter are configured to engage with each other to rotationally fix the dilation catheter relative to the guide member.

Example 4

The dilation catheter system of Example 3, wherein the first alignment feature of the guide member comprises a cavity having a non-circular cross-sectional shape, wherein the second alignment feature comprises an elongate member having a non-circular cross-sectional shape, wherein the cross-sectional shape of the cavity corresponds to the cross-sectional shape of the elongate member such that the elongate member is insertable into the cavity.

Example 5

The dilation catheter system of Example 4, wherein the first alignment feature of the guide member comprises a keyway, wherein the second alignment feature of the dilation catheter comprises a key.

Example 6

The dilation catheter system of any one or more of Examples 1 through 5, wherein the image sensor is located distal to the expandable dilator.

Example 7

The dilation catheter system of any one or more of Examples 1 through 6, wherein the dilation catheter includes a round distal tip, wherein the round distal tip is distal to the expandable dilator.

Example 8

The dilation catheter system of Example 7, wherein the image sensor is located in the round distal tip.

Example 9

The dilation catheter system of any one or more of Examples 7 through 8, wherein the round distal tip includes at least one vent opening configured to provide ventilation through the dilation catheter.

Example 10

The dilation catheter system of any one or more of Examples 1 through 9, further comprising at least one illumination source.

Example 11

The dilation catheter system of Example 10, wherein the at least one illumination source comprises a light emitting diode.

Example 12

The dilation catheter system of any one or more of Examples 10 through 11, wherein the at least one illumination source comprises an illuminating fiber.

Example 13

The dilation catheter system of any one or more of Examples 10 through 12, wherein the at least one illumination source is configured to project light distally relative to the dilation catheter, thereby illuminating a field of view of the image sensor.

Example 14

The dilation catheter system of any one or more of Examples 1 through 13, wherein the guide member comprises a guide catheter defining a lumen, wherein the dilation catheter is slidably disposed in the lumen of the guide catheter.

Example 15

The dilation catheter system of any one or more of Examples 1 through 14, wherein the dilation catheter has a flexible distal section, wherein the expandable dilator and the image sensor are located in the flexible distal section.

Example 16

A catheter system, wherein the catheter system comprises: (a) a guide member, wherein the guide member comprises a shaft, wherein the shaft includes at least one lumen extending longitudinally through the shaft; and (b) a working instrument, wherein the working instrument is insertable into the lumen of the guide member, wherein the working instrument comprises: (i) a distal end, wherein the distal end is sized to fit within one or both of a Eustachian tube or a passageway associated with a paranasal sinus, (ii) a proximal end, and (iii) an image sensor, wherein the image sensor is disposed on the distal end of the working instrument.

Example 17

The catheter system of Example 16, wherein the working instrument further comprises an actuator, wherein the actuator includes an alignment feature, wherein the alignment feature is configured to engage at least a portion of the guide member to prevent at least a portion of the working instrument from rotating relative to the guide member, wherein the alignment feature of the actuator is further configured to permit translation of the working instrument relative to the guide member when the alignment feature is engaged with the at least a portion of the guide member.

Example 18

The catheter system of any one or more of Examples 16 through 17, wherein the working instrument further comprises an expandable dilator, wherein the expandable dilator is proximal to the image sensor.

Example 19

A method of using a dilation catheter system, wherein the dilation catheter system comprises a guide member and a dilation catheter, wherein the guide member is configured to slidably receive the dilation catheter, wherein the dilation catheter includes an image sensor and an alignment feature, wherein the alignment feature is configured to engage with at an alignment feature of the guide member to prevent rotation of the dilation catheter relative to the guide member, wherein the dilation catheter further comprises an expandable dilator, wherein the method comprises: (a) inserting the guide member into a nostril of a patient; (b) advancing the guide member toward a passageway in the nasal cavity or nasopharynx; (c) viewing the passageway via the image sensor; (d) advancing the dilation catheter into the passageway, wherein the alignment feature of the dilation catheter is engaged with the alignment feature of the guide member during the act of advancing the dilation catheter into the passageway; and (e) expanding the dilator of the dilation catheter within the passageway.

Example 20

The method of Example 19, wherein the passageway comprises a Eustachian tube.

V. Miscellaneous

While guide catheter (400) and dilation catheter (500) are described above as being used to dilate the Eustachian tube (26), it should be understood that guide catheter (400) and dilation catheter (500) may be readily modified or otherwise used to provide dilation associated with paranasal sinuses. By way of example only, guide catheter (400) and dilation catheter (500) may be used to dilate a maxillary sinus ostium, a sphenoid sinus ostium, one or more openings associated with one or more ethmoid sinus air cells, the frontal recess, and/or other passageways associated with paranasal sinuses. Various suitable ways in which guide catheter (400) and/or dilation catheter (500) may be modified or otherwise used to dilate a maxillary sinus ostium, a sphenoid sinus ostium, one or more openings associated with one or more ethmoid sinus air cells, the frontal recess, and/or other passageways associated with paranasal sinuses will be apparent to those of ordinary skill in the art in view of the teachings herein.

It should be understood that the presence of keyway (452) and key (526) may ensure that the operator of dilation catheter (500) understands the angular orientation of image sensor (560) about the longitudinal axis of shafts (402, 502). Knowing the angular orientation of image sensor (560) about the longitudinal axis of shafts (402, 502) may provide the operator with a better sense of the positioning of tip (512) in relation to bend (422). Otherwise, the operator may become disoriented when viewing images from image sensor (560). Thus, keyway (452) and key (526) may provide the operator with indication and/or operational consistency in the angular orientation of image sensor (560) about the longitudinal axis of shafts (402, 502). Since key (526) only fits in keyway (452) at one angular orientation, keyway (452) and key (526) provide a poke-yoke feature. However, it should be understood that other features may be used to provide the operator with feedback indicating the angular orientation of image sensor (560) about the longitudinal axis of shafts (402, 502). By way of example only, actuator (510) may include a visual marker that the operator should match with a corresponding visual marker on proximal end (434) of hub (432). When the visual markers are angularly aligned with each other, the operator will know the angular orientation of image sensor (560) about the longitudinal axis of shaft (402). Still other suitable ways in which the operator may be provided with indication and/or operational consistency in the angular orientation of image sensor (560) about the longitudinal axis of shafts (402, 502) will be apparent to those of ordinary skill in the art in view of the teachings herein.

In some variations, guide catheter (400) includes an integral image sensor and/or illuminating feature. By way of example only, guide catheter (400) may be constructed and operable in accordance with at least some of the teachings of U.S. Provisional Patent App. No. 62/140,104, entitled "Guide Catheter with Image Capture and Light Emission Features," filed Mar. 30, 2015, the disclosure of which is incorporated by reference herein. In versions where guide catheter (400) and a dilation catheter (500) with an integral image sensor are used together, the optics associated with the image sensors (560) may be configured such that the optics associated with the image sensor of guide catheter (400) provides a focal length and/or depth of field different from the focal length and/or depth of field provided by the optics associated with image sensor (560) of dilation catheter (500). Various suitable focal lengths and depths of field, as well as the optical elements that may provide such focal lengths and depths of field, will be apparent to those of ordinary skill in the art in view of the teachings herein.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A dilation catheter system, wherein the dilation catheter system comprises:
    (a) a guide catheter, wherein the guide catheter includes:
        (i) a proximal hub, and
        (ii) a guide catheter shaft extending distally from the proximal hub, wherein the guide catheter shaft comprises a distal end and a proximal end, wherein the guide catheter shaft defines a longitudinal axis and a guide lumen extending between the distal and proximal ends; and
    (b) a dilation catheter slidably disposed within the guide lumen, wherein the dilation catheter comprises:
        (i) an elongate dilation catheter shaft having an outer diameter, wherein the dilation catheter shaft includes:
            (A) a working lumen,
            (B) an inflation lumen, wherein the inflation lumen is isolated and spaced from the working lumen, (C) a first access lumen, wherein the first access lumen is isolated and spaced from the inflation lumen and the working lumen, and (D) a second access lumen, wherein the second access lumen is isolated and spaced from the first access lumen, the inflation lumen, and the working lumen, (ii) an expandable dilator coupled to the dilation catheter shaft, wherein the expandable dilator is sized to fit within one or both of a Eustachian tube or a passageway associated with a paranasal sinus, wherein an interior of the expandable dilator is in communication with the inflation lumen, (iii) a bulbous distal tip arranged at a distal end of the dilation catheter shaft, wherein the bulbous distal tip is distal to the expandable dilator, wherein the bulbous distal tip is sized greater than the outer diameter of the dilation catheter shaft such that the bulbous distal tip is configured to prevent the dilation catheter from passing through an isthmus of a Eustachian tube, wherein the bulbous distal tip includes:

(A) an image sensor positioned in a distal end of the first access lumen, wherein the image sensor is configured to provide visualization within anatomy of a patient, wherein the image sensor is integral with the dilation catheter, (B) a light emitting feature spaced from the image sensor and positioned in a distal end of the second access lumen, and (C) first and second vent openings that communicate with the working lumen, wherein the vent openings and the working lumen are configured to permit passage of air between proximal and distal ends of the dilation catheter, (iv) an electrical wire arranged within the first access channel, wherein the electrical wire is coupled to the image sensor, and (v) one of a second electrical wire or an illumination fiber arranged within the second access channel and in operative communication with the light emitting feature.

2. The dilation catheter system of claim 1, wherein the dilation catheter further comprises an actuator coupled to a proximal portion of the dilation catheter shaft, wherein a distal extension member of the actuator is configured to be received within the guide lumen, wherein the proximal hub of the guide catheter includes a first alignment feature, wherein the distal extension member of the actuator includes a second alignment feature configured to engage the first alignment feature to rotationally fix the dilation catheter relative to the guide catheter.

3. The dilation catheter system of claim 2, wherein the first alignment feature of the guide catheter comprises a cavity having a non-circular cross-sectional shape, wherein the second alignment feature of the dilation catheter comprises an elongate member having a non-circular cross-sectional shape, wherein the cross-sectional shape of the cavity corresponds to the cross-sectional shape of the elongate member such that the elongate member is insertable into the cavity.

4. The dilation catheter system of claim 2, wherein the first alignment feature of the guide catheter comprises a keyway, wherein the second alignment feature of the dilation catheter comprises a key.

5. The dilation catheter system of claim 4, wherein the key is insertable distally into the keyway so as to permit translation of the dilation catheter relative to the guide catheter while preventing relative rotation therebetween.

6. The dilation catheter system of claim 1, wherein the light emitting feature comprises a light emitting diode.

7. The dilation catheter system of claim 1, wherein the light emitting feature comprises an illuminating fiber.

8. The dilation catheter system of claim 1, wherein the light emitting feature is configured to project light distally relative to the dilation catheter, thereby illuminating a field of view of the image sensor.

9. The dilation catheter system of claim 1, wherein each of the first and second vent openings is spaced from the image sensor and the light emitting feature.

10. The dilation catheter system of claim 1, wherein the guide catheter shaft includes a preformed bend located proximally of the distal end of the guide catheter shaft.

11. The dilation catheter system of claim 1, wherein the dilation catheter shaft further includes a flexible distal shaft portion, wherein the expandable dilator is coupled to the flexible distal shaft portion.

* * * * *